(12) United States Patent
Worrell et al.

(10) Patent No.: US 10,646,269 B2
(45) Date of Patent: May 12, 2020

(54) NON-LINEAR JAW GAP FOR ELECTROSURGICAL INSTRUMENTS

(71) Applicant: Ethicon Endo-Surgery, LLC, Guaynabo, PR (US)

(72) Inventors: Barry C. Worrell, Centerville, OH (US); Ellen M. Nienhaus, Cincinnati, OH (US); Gregory D. Bishop, Hamilton, OH (US)

(73) Assignee: Ethicon LLC, Guaynabo, PR (US)

(*) Notice: Subject to any disclaimer, the term of this patent is extended or adjusted under 35 U.S.C. 154(b) by 230 days.

(21) Appl. No.: 15/142,425

(22) Filed: Apr. 29, 2016

(65) Prior Publication Data
US 2017/0312015 A1 Nov. 2, 2017

(51) Int. Cl.
*A61B 18/14* (2006.01)
*A61B 17/00* (2006.01)
(Continued)

(52) U.S. Cl.
CPC ...... *A61B 18/1445* (2013.01); *A61B 18/1442* (2013.01); *A61B 18/1206* (2013.01); (Continued)

(58) Field of Classification Search
CPC ............ A61B 18/1445; A61B 18/1442; A61B 2018/00589; A61B 2018/0063; A61B 2018/00077
See application file for complete search history.

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| AU | 2010273651 B2 | 12/2015 |

(Continued)

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).

(Continued)

*Primary Examiner* — Michael F Peffley
*Assistant Examiner* — Amanda L Zink

(57) ABSTRACT

An end effector for an electrosurgical instrument is disclosed which comprises a first jaw comprising a first energy delivery surface, a first distal end, and a first proximal end; and a second jaw comprising a second energy delivery surface, a second distal end, and a second proximal end, wherein the first energy delivery surface comprises a first curved portion that is outwardly curved, and the second energy delivery surface comprises a second curved portion that is inwardly curved. The first jaw or the second jaw is configured for pivotal movement between an open position and a closed position. In the open position, the first and second distal ends are separated apart. In the closed position, the first and second distal ends are in proximity. The end effector also comprises an electrically conductive member which protrudes from either the first or second jaw.

19 Claims, 8 Drawing Sheets

(51) Int. Cl.
- *A61B 18/00* (2006.01)
- *A61B 90/00* (2016.01)
- *A61B 18/12* (2006.01)

(52) U.S. Cl.
CPC .............. *A61B 2017/00526* (2013.01); *A61B 2018/00053* (2013.01); *A61B 2018/0063* (2013.01); *A61B 2018/00755* (2013.01); *A61B 2018/126* (2013.01); *A61B 2018/1455* (2013.01); *A61B 2090/034* (2016.02)

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A * | 10/1982 | Cosman .................. A61B 17/30 606/42 |
| 4,409,981 A | 10/1983 | Lundberg |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |

(56) References Cited

U.S. PATENT DOCUMENTS

| | | | |
|---|---|---|---|
| 4,979,952 A | 12/1990 | Kubota et al. | |
| 4,981,756 A | 1/1991 | Rhandhawa | |
| 5,001,649 A | 3/1991 | Lo et al. | |
| 5,009,661 A * | 4/1991 | Michelson | A61B 17/1608 606/170 |
| 5,013,956 A | 5/1991 | Kurozumi et al. | |
| 5,015,227 A | 5/1991 | Broadwin et al. | |
| 5,020,514 A | 6/1991 | Heckele | |
| 5,026,370 A | 6/1991 | Lottick | |
| 5,026,387 A | 6/1991 | Thomas | |
| 5,035,695 A | 7/1991 | Weber, Jr. et al. | |
| 5,042,461 A | 8/1991 | Inoue et al. | |
| 5,042,707 A | 8/1991 | Taheri | |
| 5,061,269 A | 10/1991 | Muller | |
| 5,075,839 A | 12/1991 | Fisher et al. | |
| 5,084,052 A | 1/1992 | Jacobs | |
| 5,099,840 A | 3/1992 | Goble et al. | |
| 5,104,025 A | 4/1992 | Main et al. | |
| 5,105,117 A | 4/1992 | Yamaguchi | |
| 5,106,538 A | 4/1992 | Barma et al. | |
| 5,108,383 A | 4/1992 | White | |
| 5,109,819 A | 5/1992 | Custer et al. | |
| 5,112,300 A | 5/1992 | Ureche | |
| 5,113,139 A | 5/1992 | Furukawa | |
| 5,123,903 A | 6/1992 | Quaid et al. | |
| 5,126,618 A | 6/1992 | Takahashi et al. | |
| D327,872 S | 7/1992 | McMills et al. | |
| 5,152,762 A | 10/1992 | McElhenney | |
| 5,156,633 A | 10/1992 | Smith | |
| 5,160,334 A | 11/1992 | Billings et al. | |
| 5,162,044 A | 11/1992 | Gahn et al. | |
| 5,163,421 A | 11/1992 | Bernstein et al. | |
| 5,163,537 A | 11/1992 | Radev | |
| 5,163,945 A | 11/1992 | Ortiz et al. | |
| 5,167,619 A | 12/1992 | Wuchinich | |
| 5,167,725 A | 12/1992 | Clark et al. | |
| 5,172,344 A | 12/1992 | Ehrlich | |
| 5,174,276 A | 12/1992 | Crockard | |
| D332,660 S | 1/1993 | Rawson et al. | |
| 5,176,677 A | 1/1993 | Wuchinich | |
| 5,176,695 A | 1/1993 | Dulebohn | |
| 5,184,605 A | 2/1993 | Grzeszykowski | |
| 5,188,102 A | 2/1993 | Idemoto et al. | |
| D334,173 S | 3/1993 | Liu et al. | |
| 5,190,517 A | 3/1993 | Zieve et al. | |
| 5,190,518 A | 3/1993 | Takasu | |
| 5,190,541 A | 3/1993 | Abele et al. | |
| 5,196,007 A | 3/1993 | Ellman et al. | |
| 5,205,459 A | 4/1993 | Brinkerhoff et al. | |
| 5,205,817 A | 4/1993 | Idemoto et al. | |
| 5,209,719 A | 5/1993 | Baruch et al. | |
| 5,213,569 A | 5/1993 | Davis | |
| 5,214,339 A | 5/1993 | Naito | |
| 5,217,460 A * | 6/1993 | Knoepfler | A61B 17/29 606/1 |
| 5,218,529 A | 6/1993 | Meyer et al. | |
| 5,221,282 A | 6/1993 | Wuchinich | |
| 5,222,937 A | 6/1993 | Kagawa | |
| 5,226,909 A | 7/1993 | Evans et al. | |
| 5,226,910 A | 7/1993 | Kajiyama et al. | |
| 5,231,989 A | 8/1993 | Middleman et al. | |
| 5,234,428 A | 8/1993 | Kaufman | |
| 5,241,236 A | 8/1993 | Sasaki et al. | |
| 5,241,968 A | 9/1993 | Slater | |
| 5,242,339 A | 9/1993 | Thornton | |
| 5,242,460 A | 9/1993 | Klein et al. | |
| 5,246,003 A | 9/1993 | DeLonzor | |
| 5,254,129 A | 10/1993 | Alexander | |
| 5,257,988 A | 11/1993 | L'Esperance, Jr. | |
| 5,258,004 A | 11/1993 | Bales et al. | |
| 5,258,006 A | 11/1993 | Rydell et al. | |
| 5,261,922 A | 11/1993 | Hood | |
| 5,263,957 A | 11/1993 | Davison | |
| 5,264,925 A | 11/1993 | Shipp et al. | |
| 5,269,297 A | 12/1993 | Weng et al. | |
| 5,275,166 A | 1/1994 | Vaitekunas et al. | |
| 5,275,607 A | 1/1994 | Lo et al. | |
| 5,275,609 A | 1/1994 | Pingleton et al. | |
| 5,282,800 A | 2/1994 | Foshee et al. | |
| 5,282,817 A | 2/1994 | Hoogeboom et al. | |
| 5,285,795 A | 2/1994 | Ryan et al. | |
| 5,285,945 A | 2/1994 | Brinkerhoff et al. | |
| 5,290,286 A | 3/1994 | Parins | |
| 5,293,863 A | 3/1994 | Zhu et al. | |
| 5,300,068 A | 4/1994 | Rosar et al. | |
| 5,304,115 A | 4/1994 | Pflueger et al. | |
| D347,474 S | 5/1994 | Olson | |
| 5,307,976 A | 5/1994 | Olson et al. | |
| 5,309,927 A | 5/1994 | Welch | |
| 5,312,023 A | 5/1994 | Green et al. | |
| 5,312,425 A | 5/1994 | Evans et al. | |
| 5,318,525 A | 6/1994 | West et al. | |
| 5,318,563 A | 6/1994 | Malis et al. | |
| 5,318,564 A | 6/1994 | Eggers | |
| 5,318,570 A | 6/1994 | Hood et al. | |
| 5,318,589 A | 6/1994 | Lichtman | |
| 5,322,055 A | 6/1994 | Davison et al. | |
| 5,324,299 A | 6/1994 | Davison et al. | |
| 5,326,013 A | 7/1994 | Green et al. | |
| 5,326,342 A | 7/1994 | Pflueger et al. | |
| 5,330,471 A | 7/1994 | Eggers | |
| 5,330,502 A | 7/1994 | Hassler et al. | |
| 5,334,183 A | 8/1994 | Wuchinich | |
| 5,339,723 A | 8/1994 | Huitema | |
| 5,342,356 A | 8/1994 | Ellman et al. | |
| 5,342,359 A | 8/1994 | Rydell | |
| 5,344,420 A | 9/1994 | Hilal et al. | |
| 5,345,937 A | 9/1994 | Middleman et al. | |
| 5,346,502 A | 9/1994 | Estabrook et al. | |
| 5,353,474 A | 10/1994 | Good et al. | |
| 5,357,164 A | 10/1994 | Imabayashi et al. | |
| 5,357,423 A | 10/1994 | Weaver et al. | |
| 5,359,994 A | 11/1994 | Krauter et al. | |
| 5,361,583 A | 11/1994 | Huitema | |
| 5,366,466 A | 11/1994 | Christian et al. | |
| 5,368,557 A | 11/1994 | Nita et al. | |
| 5,370,645 A | 12/1994 | Klicek et al. | |
| 5,371,429 A | 12/1994 | Manna | |
| 5,374,813 A | 12/1994 | Shipp | |
| D354,564 S | 1/1995 | Medema | |
| 5,381,067 A | 1/1995 | Greenstein et al. | |
| 5,383,874 A | 1/1995 | Jackson et al. | |
| 5,387,207 A | 2/1995 | Dyer et al. | |
| 5,387,215 A | 2/1995 | Fisher | |
| 5,389,098 A | 2/1995 | Tsuruta et al. | |
| 5,394,187 A | 2/1995 | Shipp | |
| 5,395,033 A | 3/1995 | Byrne et al. | |
| 5,395,312 A | 3/1995 | Desai | |
| 5,395,363 A | 3/1995 | Billings et al. | |
| 5,395,364 A | 3/1995 | Anderhub et al. | |
| 5,396,266 A | 3/1995 | Brimhall | |
| 5,396,900 A | 3/1995 | Slater et al. | |
| 5,400,267 A | 3/1995 | Denen et al. | |
| 5,403,312 A | 4/1995 | Yates et al. | |
| 5,403,334 A | 4/1995 | Evans et al. | |
| 5,406,503 A | 4/1995 | Williams, Jr. et al. | |
| 5,408,268 A | 4/1995 | Shipp | |
| D358,887 S | 5/1995 | Feinberg | |
| 5,411,481 A | 5/1995 | Allen et al. | |
| 5,417,709 A | 5/1995 | Slater | |
| 5,419,761 A | 5/1995 | Narayanan et al. | |
| 5,421,829 A | 6/1995 | Olichney et al. | |
| 5,423,844 A | 6/1995 | Miller | |
| 5,428,504 A | 6/1995 | Bhatla | |
| 5,429,131 A | 7/1995 | Scheinman et al. | |
| 5,438,997 A | 8/1995 | Sieben et al. | |
| 5,441,499 A | 8/1995 | Fritzsch | |
| 5,443,463 A | 8/1995 | Stern et al. | |
| 5,445,638 A | 8/1995 | Rydell et al. | |
| 5,445,639 A | 8/1995 | Kuslich et al. | |
| 5,447,509 A | 9/1995 | Mills et al. | |
| 5,449,370 A | 9/1995 | Vaitekunas | |
| 5,451,053 A | 9/1995 | Garrido | |
| 5,451,161 A | 9/1995 | Sharp | |

(56) References Cited

U.S. PATENT DOCUMENTS

| | | |
|---|---|---|
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A * | 5/1997 | Schulze ............ A61B 17/07207 227/176.1 |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A * | 11/1997 | Yates ............... A61B 17/07207 606/41 |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |

(56) References Cited

U.S. PATENT DOCUMENTS

| | | |
|---|---|---|
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A * | 5/1999 | Bito .................. A61B 17/122 606/139 |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H001904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 * | 2/2001 | Buysse .............. A61B 17/2816 30/342 |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |

(56) References Cited

U.S. PATENT DOCUMENTS

| | | |
|---|---|---|
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H002037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B2 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |

(56) References Cited

U.S. PATENT DOCUMENTS

| | | |
|---|---|---|
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 * | 5/2004 | Yamauchi .......... A61B 18/1442 606/37 |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 * | 8/2005 | Hooven .......... A61B 18/1445 606/41 |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |

(56) References Cited

U.S. PATENT DOCUMENTS

| | | |
|---|---|---|
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |

(56) References Cited

U.S. PATENT DOCUMENTS

| | | |
|---|---|---|
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |

(56) References Cited

U.S. PATENT DOCUMENTS

| | | |
|---|---|---|
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Likura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,020,743 B2 | 9/2011 | Shelton, IV |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |

(56) References Cited

U.S. PATENT DOCUMENTS

| | | |
|---|---|---|
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Homer |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |

(56) References Cited

U.S. PATENT DOCUMENTS

| | | | |
|---|---|---|---|
| 8,562,600 B2 | 10/2013 | Kirkpatrick et al. | |
| 8,562,604 B2 | 10/2013 | Nishimura | |
| 8,568,390 B2 | 10/2013 | Mueller | |
| 8,568,397 B2 | 10/2013 | Horner et al. | |
| 8,568,400 B2 | 10/2013 | Gilbert | |
| 8,568,412 B2 * | 10/2013 | Brandt | A61B 18/1445 606/205 |
| 8,569,997 B2 | 10/2013 | Lee | |
| 8,573,461 B2 | 11/2013 | Shelton, IV et al. | |
| 8,573,465 B2 | 11/2013 | Shelton, IV | |
| 8,574,231 B2 | 11/2013 | Boudreaux et al. | |
| 8,574,253 B2 | 11/2013 | Gruber et al. | |
| 8,579,176 B2 | 11/2013 | Smith et al. | |
| 8,579,897 B2 | 11/2013 | Vakharia et al. | |
| 8,579,928 B2 | 11/2013 | Robertson et al. | |
| 8,579,937 B2 | 11/2013 | Gresham | |
| 8,585,727 B2 | 11/2013 | Polo | |
| 8,588,371 B2 | 11/2013 | Ogawa et al. | |
| 8,591,459 B2 | 11/2013 | Clymer et al. | |
| 8,591,506 B2 | 11/2013 | Wham et al. | |
| 8,591,536 B2 | 11/2013 | Robertson | |
| D695,407 S | 12/2013 | Price et al. | |
| D696,631 S | 12/2013 | Price et al. | |
| 8,596,513 B2 | 12/2013 | Olson et al. | |
| 8,597,193 B2 | 12/2013 | Grunwald et al. | |
| 8,602,031 B2 | 12/2013 | Reis et al. | |
| 8,602,288 B2 | 12/2013 | Shelton, IV et al. | |
| 8,603,089 B2 | 12/2013 | Viola | |
| 8,608,044 B2 | 12/2013 | Hueil et al. | |
| 8,608,045 B2 | 12/2013 | Smith et al. | |
| 8,608,745 B2 | 12/2013 | Guzman et al. | |
| 8,613,383 B2 | 12/2013 | Beckman et al. | |
| 8,616,431 B2 | 12/2013 | Timm et al. | |
| 8,617,152 B2 | 12/2013 | Werneth et al. | |
| 8,617,194 B2 | 12/2013 | Beaupre | |
| 8,622,274 B2 | 1/2014 | Yates et al. | |
| 8,623,011 B2 | 1/2014 | Spivey | |
| 8,623,016 B2 | 1/2014 | Fischer | |
| 8,623,027 B2 | 1/2014 | Price et al. | |
| 8,623,044 B2 | 1/2014 | Timm et al. | |
| 8,628,529 B2 | 1/2014 | Aldridge et al. | |
| 8,628,534 B2 | 1/2014 | Jones et al. | |
| 8,632,461 B2 | 1/2014 | Glossop | |
| 8,636,736 B2 | 1/2014 | Yates et al. | |
| 8,638,428 B2 | 1/2014 | Brown | |
| 8,640,788 B2 | 2/2014 | Dachs, II et al. | |
| 8,641,663 B2 | 2/2014 | Kirschenman et al. | |
| 8,647,350 B2 | 2/2014 | Mohan et al. | |
| 8,650,728 B2 | 2/2014 | Wan et al. | |
| 8,652,120 B2 | 2/2014 | Giordano et al. | |
| 8,652,132 B2 | 2/2014 | Tsuchiya et al. | |
| 8,652,155 B2 | 2/2014 | Houser et al. | |
| 8,657,489 B2 | 2/2014 | Ladurner et al. | |
| 8,659,208 B1 | 2/2014 | Rose et al. | |
| 8,663,220 B2 | 3/2014 | Wiener et al. | |
| 8,663,222 B2 | 3/2014 | Anderson et al. | |
| 8,663,223 B2 | 3/2014 | Masuda et al. | |
| 8,663,262 B2 | 3/2014 | Smith et al. | |
| 8,668,691 B2 | 3/2014 | Heard | |
| 8,668,710 B2 | 3/2014 | Slipszenko et al. | |
| 8,684,253 B2 | 4/2014 | Giordano et al. | |
| 8,685,016 B2 | 4/2014 | Wham et al. | |
| 8,685,020 B2 | 4/2014 | Weizman et al. | |
| 8,690,582 B2 | 4/2014 | Rohrbach et al. | |
| 8,695,866 B2 | 4/2014 | Leimbach et al. | |
| 8,696,366 B2 | 4/2014 | Chen et al. | |
| 8,696,665 B2 | 4/2014 | Hunt et al. | |
| 8,696,666 B2 | 4/2014 | Sanai et al. | |
| 8,702,609 B2 | 4/2014 | Hadjicostis | |
| 8,702,704 B2 | 4/2014 | Shelton, IV et al. | |
| 8,704,425 B2 | 4/2014 | Giordano et al. | |
| 8,708,213 B2 | 4/2014 | Shelton, IV et al. | |
| 8,709,031 B2 | 4/2014 | Stulen | |
| 8,709,035 B2 | 4/2014 | Johnson et al. | |
| 8,715,270 B2 | 5/2014 | Weitzner et al. | |
| 8,715,277 B2 | 5/2014 | Weizman | |
| 8,721,640 B2 | 5/2014 | Taylor et al. | |
| 8,721,657 B2 | 5/2014 | Kondoh et al. | |
| 8,733,613 B2 | 5/2014 | Huitema et al. | |
| 8,734,443 B2 | 5/2014 | Hixson et al. | |
| 8,747,238 B2 | 6/2014 | Shelton, IV et al. | |
| 8,747,351 B2 | 6/2014 | Schultz | |
| 8,747,404 B2 | 6/2014 | Boudreaux et al. | |
| 8,749,116 B2 | 6/2014 | Messerly et al. | |
| 8,752,264 B2 | 6/2014 | Ackley et al. | |
| 8,752,749 B2 | 6/2014 | Moore et al. | |
| 8,753,338 B2 | 6/2014 | Widenhouse et al. | |
| 8,754,570 B2 | 6/2014 | Voegele et al. | |
| 8,758,342 B2 | 6/2014 | Bales et al. | |
| 8,758,352 B2 | 6/2014 | Cooper et al. | |
| 8,758,391 B2 | 6/2014 | Swayze et al. | |
| 8,764,735 B2 | 7/2014 | Coe et al. | |
| 8,764,747 B2 | 7/2014 | Cummings et al. | |
| 8,767,970 B2 | 7/2014 | Eppolito | |
| 8,770,459 B2 | 7/2014 | Racenet et al. | |
| 8,771,269 B2 | 7/2014 | Sherman et al. | |
| 8,771,270 B2 | 7/2014 | Burbank | |
| 8,771,293 B2 | 7/2014 | Surti et al. | |
| 8,773,001 B2 | 7/2014 | Wiener et al. | |
| 8,777,944 B2 | 7/2014 | Frankhouser et al. | |
| 8,777,945 B2 | 7/2014 | Floume et al. | |
| 8,779,648 B2 | 7/2014 | Giordano et al. | |
| 8,783,541 B2 | 7/2014 | Shelton, IV et al. | |
| 8,784,415 B2 | 7/2014 | Malackowski et al. | |
| 8,784,418 B2 | 7/2014 | Romero | |
| 8,790,342 B2 | 7/2014 | Stulen et al. | |
| 8,795,274 B2 | 8/2014 | Hanna | |
| 8,795,276 B2 | 8/2014 | Dietz et al. | |
| 8,795,327 B2 | 8/2014 | Dietz et al. | |
| 8,800,838 B2 | 8/2014 | Shelton, IV | |
| 8,801,710 B2 | 8/2014 | Ullrich et al. | |
| 8,801,752 B2 | 8/2014 | Fortier et al. | |
| 8,808,204 B2 | 8/2014 | Irisawa et al. | |
| 8,808,319 B2 | 8/2014 | Houser et al. | |
| 8,814,856 B2 | 8/2014 | Elmouelhi et al. | |
| 8,814,870 B2 | 8/2014 | Paraschiv et al. | |
| 8,820,605 B2 | 9/2014 | Shelton, IV | |
| 8,821,388 B2 | 9/2014 | Naito et al. | |
| 8,827,992 B2 | 9/2014 | Koss et al. | |
| 8,827,995 B2 | 9/2014 | Schaller et al. | |
| 8,834,466 B2 | 9/2014 | Cummings et al. | |
| 8,834,518 B2 | 9/2014 | Faller et al. | |
| 8,844,789 B2 | 9/2014 | Shelton, IV et al. | |
| 8,845,537 B2 | 9/2014 | Tanaka et al. | |
| 8,845,630 B2 | 9/2014 | Mehta et al. | |
| 8,848,808 B2 | 9/2014 | Dress | |
| 8,851,354 B2 | 10/2014 | Swensgard et al. | |
| 8,852,184 B2 | 10/2014 | Kucklick | |
| 8,858,547 B2 | 10/2014 | Brogna | |
| 8,862,955 B2 | 10/2014 | Cesari | |
| 8,864,749 B2 | 10/2014 | Okada | |
| 8,864,757 B2 | 10/2014 | Klimovitch et al. | |
| 8,864,761 B2 | 10/2014 | Johnson et al. | |
| 8,870,865 B2 | 10/2014 | Frankhouser et al. | |
| 8,876,726 B2 | 11/2014 | Amit et al. | |
| 8,876,858 B2 | 11/2014 | Braun | |
| 8,882,766 B2 | 11/2014 | Couture et al. | |
| 8,882,791 B2 | 11/2014 | Stulen | |
| 8,888,776 B2 | 11/2014 | Dietz et al. | |
| 8,888,783 B2 | 11/2014 | Young | |
| 8,888,809 B2 | 11/2014 | Davison et al. | |
| 8,899,462 B2 | 12/2014 | Kostrzewski et al. | |
| 8,900,259 B2 | 12/2014 | Houser et al. | |
| 8,906,016 B2 | 12/2014 | Boudreaux et al. | |
| 8,906,017 B2 | 12/2014 | Rioux et al. | |
| 8,911,438 B2 | 12/2014 | Swoyer et al. | |
| 8,911,460 B2 | 12/2014 | Neurohr et al. | |
| 8,920,412 B2 | 12/2014 | Fritz et al. | |
| 8,920,414 B2 | 12/2014 | Stone et al. | |
| 8,920,421 B2 | 12/2014 | Rupp | |
| 8,926,607 B2 | 1/2015 | Norvell et al. | |
| 8,926,608 B2 | 1/2015 | Bacher et al. | |
| 8,926,620 B2 | 1/2015 | Chasmawala et al. | |
| 8,931,682 B2 | 1/2015 | Timm et al. | |

(56) References Cited

U.S. PATENT DOCUMENTS

| | | |
|---|---|---|
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,695 B2 | 5/2015 | Giordano et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |

(56) References Cited

U.S. PATENT DOCUMENTS

| | | |
|---|---|---|
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,690,362 B2 | 6/2017 | Leimbach et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,246 B2 | 11/2017 | Shelton, IV et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |

(56) References Cited

U.S. PATENT DOCUMENTS

| | | |
|---|---|---|
| 9,949,788 B2 | 4/2018 | Boudreaux |
| 9,962,182 B2 | 5/2018 | Dietz et al. |
| 9,974,539 B2 | 5/2018 | Yates et al. |
| 9,987,033 B2 | 6/2018 | Neurohr et al. |
| 10,004,526 B2 | 6/2018 | Dycus et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,070,916 B2 | 9/2018 | Artale |
| 10,080,609 B2 | 9/2018 | Hancock et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,111,703 B2 | 10/2018 | Cosman, Jr. et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,172,665 B2 | 1/2019 | Heckel et al. |
| 10,448,986 B2 | 10/2019 | Zikorus et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033280 A1 | 2/2005 | Francischelli et al. |
| 2005/0033337 A1 | 2/2005 | Muir et al. |
| 2005/0070800 A1 | 3/2005 | Takahashi |
| 2005/0088285 A1 | 4/2005 | Jei |
| 2005/0090817 A1* | 4/2005 | Phan ............... A61B 18/1445 606/41 |
| 2005/0096683 A1 | 5/2005 | Ellins et al. |
| 2005/0099824 A1 | 5/2005 | Dowling et al. |
| 2005/0119654 A1 | 6/2005 | Swanson et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064085 A1* | 3/2006 | Schechter ......... A61B 18/1445 606/50 |
| 2006/0064086 A1 | 3/2006 | Odom |
| 2006/0066181 A1 | 3/2006 | Bromfield et al. |

(56) References Cited

U.S. PATENT DOCUMENTS

| | | |
|---|---|---|
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |

(56) References Cited

U.S. PATENT DOCUMENTS

| | | |
|---|---|---|
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0028964 A1 | 2/2011 | Edwards |
| 2011/0071523 A1 | 3/2011 | Dickhans |
| 2011/0087220 A1 | 4/2011 | Felder et al. |
| 2011/0106141 A1 | 5/2011 | Nakamura |
| 2011/0125149 A1 | 5/2011 | El-Galley et al. |
| 2011/0125151 A1 | 5/2011 | Strauss et al. |
| 2011/0160725 A1 | 6/2011 | Kabaya et al. |
| 2011/0238010 A1 | 9/2011 | Kirschenman et al. |
| 2011/0273465 A1 | 11/2011 | Konishi et al. |
| 2011/0276049 A1 | 11/2011 | Gerhardt |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078139 A1 | 3/2012 | Aldridge et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0211542 A1 | 8/2012 | Racenet |
| 2012/0253328 A1 | 10/2012 | Cunningham et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0338647 A1 | 12/2013 | Bacher et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0114327 A1 | 4/2014 | Boudreaux et al. |
| 2014/0121569 A1 | 5/2014 | Schafer et al. |
| 2014/0135804 A1 | 5/2014 | Weisenburgh, II et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0246475 A1 | 9/2014 | Hall et al. |
| 2014/0263541 A1 | 9/2014 | Leimbach et al. |
| 2014/0263552 A1 | 9/2014 | Hall et al. |
| 2014/0276659 A1 | 9/2014 | Juergens et al. |
| 2014/0276754 A1 | 9/2014 | Gilbert et al. |
| 2014/0276797 A1 | 9/2014 | Batchelor et al. |
| 2014/0276806 A1 | 9/2014 | Heim |
| 2014/0276970 A1 | 9/2014 | Messerly et al. |
| 2014/0330271 A1 | 11/2014 | Dietz et al. |
| 2015/0032100 A1 | 1/2015 | Coulson et al. |
| 2015/0032150 A1 | 1/2015 | Ishida et al. |
| 2015/0080876 A1 | 3/2015 | Worrell et al. |
| 2015/0080887 A1 | 3/2015 | Sobajima et al. |
| 2015/0080912 A1 | 3/2015 | Sapre |
| 2015/0088178 A1 | 3/2015 | Stulen et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182276 A1 | 7/2015 | Wiener et al. |
| 2015/0182277 A1 | 7/2015 | Wiener et al. |
| 2015/0230853 A1 | 8/2015 | Johnson et al. |
| 2015/0230861 A1 | 8/2015 | Woloszko et al. |
| 2015/0238260 A1 | 8/2015 | Nau, Jr. |
| 2015/0257780 A1 | 9/2015 | Houser |
| 2015/0272659 A1 | 10/2015 | Boudreaux et al. |
| 2015/0272660 A1 | 10/2015 | Boudreaux et al. |
| 2015/0313667 A1 | 11/2015 | Allen, IV |
| 2015/0320480 A1 | 11/2015 | Cosman, Jr. et al. |
| 2015/0320481 A1 | 11/2015 | Cosman, Jr. et al. |
| 2015/0340586 A1 | 11/2015 | Wiener et al. |
| 2016/0030076 A1 | 2/2016 | Faller et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0144204 A1 | 5/2016 | Akagane |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175032 A1 | 6/2016 | Yang |
| 2016/0199123 A1 | 7/2016 | Thomas et al. |
| 2016/0199125 A1 | 7/2016 | Jones |
| 2016/0206342 A1 | 7/2016 | Robertson et al. |
| 2016/0228171 A1 | 8/2016 | Boudreaux |
| 2016/0262786 A1 | 9/2016 | Madan et al. |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0287311 A1 | 10/2016 | Friedrichs |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0296270 A1 | 10/2016 | Strobl et al. |
| 2016/0317217 A1 | 11/2016 | Batross et al. |
| 2016/0324537 A1 | 11/2016 | Green et al. |
| 2016/0338726 A1 | 11/2016 | Stulen et al. |
| 2016/0346001 A1 | 12/2016 | Vakharia et al. |
| 2016/0367273 A1 | 12/2016 | Robertson et al. |

(56) References Cited

U.S. PATENT DOCUMENTS

| | | |
|---|---|---|
| 2016/0367281 A1 | 12/2016 | Gee et al. |
| 2016/0374708 A1 | 12/2016 | Wiener et al. |
| 2016/0374709 A1 | 12/2016 | Timm et al. |
| 2016/0374712 A1 | 12/2016 | Stulen et al. |
| 2016/0374752 A1 | 12/2016 | Hancock et al. |
| 2017/0000512 A1 | 1/2017 | Conlon et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000553 A1 | 1/2017 | Wiener et al. |
| 2017/0000554 A1 | 1/2017 | Yates et al. |
| 2017/0056056 A1 | 3/2017 | Wiener et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0090507 A1 | 3/2017 | Wiener et al. |
| 2017/0095267 A1 | 4/2017 | Messerly et al. |
| 2017/0105757 A1 | 4/2017 | Weir et al. |
| 2017/0105782 A1 | 4/2017 | Scheib et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0143371 A1 | 5/2017 | Witt et al. |
| 2017/0143877 A1 | 5/2017 | Witt et al. |
| 2017/0164994 A1 | 6/2017 | Smith |
| 2017/0189095 A1 | 7/2017 | Danziger et al. |
| 2017/0189096 A1 | 7/2017 | Danziger et al. |
| 2017/0189101 A1 | 7/2017 | Yates et al. |
| 2017/0196586 A1 | 7/2017 | Witt et al. |
| 2017/0196587 A1 | 7/2017 | Witt et al. |
| 2017/0202570 A1 | 7/2017 | Shelton, IV et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202593 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2017/0312014 A1 | 11/2017 | Strobl et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0319228 A1 | 11/2017 | Worrell et al. |
| 2017/0319265 A1 | 11/2017 | Yates et al. |
| 2017/0325874 A1 | 11/2017 | Noack et al. |
| 2017/0348064 A1 | 12/2017 | Stewart et al. |
| 2018/0014872 A1 | 1/2018 | Dickerson |
| 2018/0028257 A1 | 2/2018 | Yates et al. |
| 2018/0036061 A1 | 2/2018 | Yates et al. |
| 2018/0036065 A1 | 2/2018 | Yates et al. |
| 2018/0042658 A1 | 2/2018 | Shelton, IV et al. |
| 2018/0064961 A1 | 3/2018 | Wiener et al. |
| 2018/0078277 A1 | 3/2018 | Illizaliturri-Sanchez et al. |
| 2018/0098785 A1 | 4/2018 | Price et al. |
| 2018/0098808 A1 | 4/2018 | Yates et al. |
| 2018/0116706 A9 | 5/2018 | Wiener et al. |
| 2018/0146976 A1 | 5/2018 | Clauda et al. |
| 2018/0177545 A1 | 6/2018 | Boudreaux et al. |
| 2018/0235691 A1 | 8/2018 | Voegele et al. |
| 2018/0280083 A1 | 10/2018 | Parihar et al. |
| 2019/0021783 A1 | 1/2019 | Asher et al. |
| 2019/0105067 A1 | 4/2019 | Boudreaux et al. |
| 2019/0201048 A1 | 7/2019 | Stulen et al. |
| 2019/0209201 A1 | 7/2019 | Boudreaux et al. |
| 2019/0282288 A1 | 9/2019 | Boudreaux |
| 2019/0282292 A1 | 9/2019 | Wiener et al. |

FOREIGN PATENT DOCUMENTS

| | | |
|---|---|---|
| CA | 2535467 A1 | 4/1993 |
| CN | 1233944 A | 11/1999 |
| CN | 1253485 A | 5/2000 |
| CN | 2460047 Y | 11/2001 |
| CN | 1634601 A | 7/2005 |
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 101396300 A | 4/2009 |
| CN | 101467917 A | 7/2009 |
| CN | 101474081 A | 7/2009 |
| CN | 101674782 A | 3/2010 |
| CN | 101883531 A | 11/2010 |
| CN | 102160045 A | 8/2011 |
| CN | 202027624 U | 11/2011 |
| CN | 102834069 A | 12/2012 |
| CN | 101313865 B | 1/2013 |
| DE | 3904558 A1 | 8/1990 |
| DE | 9210327 U1 | 11/1992 |
| DE | 4300307 A1 | 7/1994 |
| DE | 4323585 A1 | 1/1995 |
| DE | 19608716 C1 | 4/1997 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EA | 2453813 A2 | 5/2012 |
| EP | 0171967 A2 | 2/1986 |
| EP | 0336742 A2 | 10/1989 |
| EP | 0136855 B1 | 11/1989 |
| EP | 0342448 A1 | 11/1989 |
| EP | 0443256 A1 | 8/1991 |
| EP | 0456470 A1 | 11/1991 |
| EP | 0238667 B1 | 2/1993 |
| EP | 0340803 B1 | 8/1993 |
| EP | 0598976 A2 | 6/1994 |
| EP | 0630612 A1 | 12/1994 |
| EP | 0424685 B1 | 5/1995 |
| EP | 0677275 A2 | 10/1995 |
| EP | 0482195 B1 | 1/1996 |
| EP | 0695535 A1 | 2/1996 |
| EP | 0705571 A1 | 4/1996 |
| EP | 0741996 B1 | 11/1996 |
| EP | 0612570 B1 | 6/1997 |
| EP | 0557806 B1 | 5/1998 |
| EP | 0640317 B1 | 9/1999 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 0722696 B1 | 12/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |

(56) References Cited

FOREIGN PATENT DOCUMENTS

| | | | |
|---|---|---|---|
| EP | 1199044 B1 | 12/2005 |
| EP | 1609428 A1 | 12/2005 |
| EP | 1199043 B1 | 3/2006 |
| EP | 1293172 B1 | 4/2006 |
| EP | 0875209 B1 | 5/2006 |
| EP | 1433425 B1 | 6/2006 |
| EP | 1256323 B1 | 8/2006 |
| EP | 1698289 A2 | 9/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1815950 A1 | 8/2007 |
| EP | 1839599 A1 | 10/2007 |
| EP | 1844720 A1 | 10/2007 |
| EP | 1862133 A1 | 12/2007 |
| EP | 1875875 A1 | 1/2008 |
| EP | 1878399 A1 | 1/2008 |
| EP | 1915953 A1 | 4/2008 |
| EP | 1532933 B1 | 5/2008 |
| EP | 1199045 B1 | 6/2008 |
| EP | 1707143 B1 | 6/2008 |
| EP | 1943957 A2 | 7/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1477104 B1 | 1/2009 |
| EP | 2014218 A2 | 1/2009 |
| EP | 1849424 B1 | 4/2009 |
| EP | 2042112 A2 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 2106758 A1 | 10/2009 |
| EP | 2111813 A1 | 10/2009 |
| EP | 2131760 A1 | 12/2009 |
| EP | 1769766 B1 | 2/2010 |
| EP | 2151204 A1 | 2/2010 |
| EP | 2153791 A1 | 2/2010 |
| EP | 2200145 A1 | 6/2010 |
| EP | 1214913 B1 | 7/2010 |
| EP | 2238938 A1 | 10/2010 |
| EP | 2243439 A1 | 10/2010 |
| EP | 2298154 A2 | 3/2011 |
| EP | 2305144 A1 | 4/2011 |
| EP | 1510178 B1 | 6/2011 |
| EP | 1946708 B1 | 6/2011 |
| EP | 2335630 A1 | 6/2011 |
| EP | 1502551 B1 | 7/2011 |
| EP | 1728475 B1 | 8/2011 |
| EP | 2353518 A1 | 8/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 1586275 B1 | 5/2013 |
| EP | 1616529 B1 | 9/2013 |
| EP | 1997438 B1 | 11/2013 |
| EP | 2668922 A1 | 12/2013 |
| EP | 2508143 B1 | 2/2014 |
| EP | 2583633 B1 | 10/2014 |
| EP | 2076195 B1 | 12/2015 |
| EP | 2113210 B1 | 3/2016 |
| EP | 2510891 B1 | 6/2016 |
| EP | 2227155 B1 | 7/2016 |
| EP | 2859858 B1 | 12/2016 |
| ES | 2115068 T3 | 6/1998 |
| GB | 1482943 A | 8/1977 |
| GB | 2032221 A | 4/1980 |
| GB | 2317566 A | 4/1998 |
| GB | 2379878 B | 11/2004 |
| GB | 2472216 A | 2/2011 |
| GB | 2447767 B | 8/2011 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04150847 A | 5/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H06217988 A | 8/1994 |
| JP | H06507081 A | 8/1994 |
| JP | H 07500514 A | 1/1995 |
| JP | H07508910 A | 10/1995 |
| JP | H07308323 A | 11/1995 |
| JP | H0824266 A | 1/1996 |
| JP | H08229050 A | 9/1996 |
| JP | H08275951 A | 10/1996 |
| JP | H08299351 A | 11/1996 |
| JP | H08336544 A | 12/1996 |
| JP | H08336545 A | 12/1996 |
| JP | H09503146 A | 3/1997 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11501543 A | 2/1999 |
| JP | H11128238 A | 5/1999 |
| JP | H11192235 A | 7/1999 |
| JP | H11253451 A | 9/1999 |
| JP | H11318918 A | 11/1999 |
| JP | 2000041991 A | 2/2000 |
| JP | 2000070279 A | 3/2000 |
| JP | 2000210299 A | 8/2000 |
| JP | 2000271145 A | 10/2000 |
| JP | 2000287987 A | 10/2000 |
| JP | 2001029353 A | 2/2001 |
| JP | 2001502216 A | 2/2001 |
| JP | 2001309925 A | 11/2001 |
| JP | 2002059380 A | 2/2002 |
| JP | 2002177295 A | 6/2002 |
| JP | 2002186901 A | 7/2002 |
| JP | 2002204808 A | 7/2002 |
| JP | 2002238919 A | 8/2002 |
| JP | 2002263579 A | 9/2002 |
| JP | 2002301086 A | 10/2002 |
| JP | 2002306504 A | 10/2002 |
| JP | 2002330977 A | 11/2002 |

(56) References Cited

FOREIGN PATENT DOCUMENTS

| | | |
|---|---|---|
| JP | 2002542690 A | 12/2002 |
| JP | 2003000612 A | 1/2003 |
| JP | 2003010201 A | 1/2003 |
| JP | 2003510158 A | 3/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003530921 A | 10/2003 |
| JP | 2003310627 A | 11/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005040222 A | 2/2005 |
| JP | 2005066316 A | 3/2005 |
| JP | 2005074088 A | 3/2005 |
| JP | 2005507679 A | 3/2005 |
| JP | 2005534451 A | 11/2005 |
| JP | 2005337119 A | 12/2005 |
| JP | 2006006410 A | 1/2006 |
| JP | 2006068396 A | 3/2006 |
| JP | 2006075376 A | 3/2006 |
| JP | 2006081664 A | 3/2006 |
| JP | 2006114072 A | 4/2006 |
| JP | 2006512149 A | 4/2006 |
| JP | 2006116194 A | 5/2006 |
| JP | 2006158525 A | 6/2006 |
| JP | 2006217716 A | 8/2006 |
| JP | 2006218296 A | 8/2006 |
| JP | 2006288431 A | 10/2006 |
| JP | 2007037568 A | 2/2007 |
| JP | 200750181 A | 3/2007 |
| JP | 2007050181 A | 3/2007 |
| JP | 2007-524459 A | 8/2007 |
| JP | 2007229454 A | 9/2007 |
| JP | 2007527747 A | 10/2007 |
| JP | 2007296369 A | 11/2007 |
| JP | 200801876 A | 1/2008 |
| JP | 2008018226 A | 1/2008 |
| JP | 200833644 A | 2/2008 |
| JP | 2008036390 A | 2/2008 |
| JP | 2008508065 A | 3/2008 |
| JP | 2008119250 A | 5/2008 |
| JP | 2008515562 A | 5/2008 |
| JP | 2008521503 A | 6/2008 |
| JP | 2008188160 A | 8/2008 |
| JP | D1339835 S | 8/2008 |
| JP | 2008212679 A | 9/2008 |
| JP | 2008536562 A | 9/2008 |
| JP | 2008284374 A | 11/2008 |
| JP | 2009511206 A | 3/2009 |
| JP | 2009082711 A | 4/2009 |
| JP | 2009517181 A | 4/2009 |
| JP | 4262923 B2 | 5/2009 |
| JP | 2009523567 A | 6/2009 |
| JP | 2009148557 A | 7/2009 |
| JP | 2009236177 A | 10/2009 |
| JP | 2009254819 A | 11/2009 |
| JP | 2010000336 A | 1/2010 |
| JP | 2010009686 A | 1/2010 |
| JP | 2010514923 A | 5/2010 |
| JP | 2010121865 A | 6/2010 |
| JP | 2010534522 A | 11/2010 |
| JP | 2010540186 A | 12/2010 |
| JP | 2011505198 A | 2/2011 |
| JP | 2012/075899 | 4/2012 |
| JP | 2012071186 A | 4/2012 |
| JP | 2012235658 A | 11/2012 |
| JP | 5208761 B2 | 6/2013 |
| JP | 5714508 B2 | 5/2015 |
| JP | 2015515339 A | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2304934 C2 | 8/2007 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9222259 A2 | 12/1992 |
| WO | WO-9307817 A1 | 4/1993 |
| WO | WO-9308757 A1 | 5/1993 |
| WO | WO-9314708 A1 | 8/1993 |
| WO | WO-9316646 A1 | 9/1993 |
| WO | WO-9320877 A1 | 10/1993 |
| WO | WO-9322973 A1 | 11/1993 |
| WO | WO-9400059 A1 | 1/1994 |
| WO | WO-9421183 A1 | 9/1994 |
| WO | WO-9424949 A1 | 11/1994 |
| WO | WO-9509572 A1 | 4/1995 |
| WO | WO-9510978 A1 | 4/1995 |
| WO | WO-9534259 A1 | 12/1995 |
| WO | WO-9630885 A1 | 10/1996 |
| WO | WO-9635382 A1 | 11/1996 |
| WO | WO-9639086 A1 | 12/1996 |
| WO | WO-9710764 A1 | 3/1997 |
| WO | WO-9800069 A1 | 1/1998 |
| WO | WO-9816156 A1 | 4/1998 |
| WO | WO-9826739 A1 | 6/1998 |
| WO | WO-9835621 A1 | 8/1998 |
| WO | WO-9837815 A1 | 9/1998 |
| WO | WO-9840020 A1 | 9/1998 |
| WO | WO-9847436 A1 | 10/1998 |
| WO | WO-9857588 A1 | 12/1998 |
| WO | WO-9920213 A1 | 4/1999 |
| WO | WO-9923960 A1 | 5/1999 |
| WO | WO-9940857 A1 | 8/1999 |
| WO | WO-9940861 A1 | 8/1999 |
| WO | WO-9952489 A1 | 10/1999 |
| WO | WO-0024330 A1 | 5/2000 |
| WO | WO-0024331 A1 | 5/2000 |
| WO | WO-0025691 A1 | 5/2000 |
| WO | WO-0064358 A2 | 11/2000 |
| WO | WO-0074585 A2 | 12/2000 |
| WO | WO-0124713 A1 | 4/2001 |
| WO | WO-0128444 A1 | 4/2001 |
| WO | WO-0154590 A1 | 8/2001 |
| WO | WO-0167970 A1 | 9/2001 |
| WO | WO-0172251 A1 | 10/2001 |
| WO | WO-0195810 A2 | 12/2001 |
| WO | WO-0224080 A2 | 3/2002 |
| WO | WO-0238057 A1 | 5/2002 |
| WO | WO-02062241 A1 | 8/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-03082133 A1 | 10/2003 |
| WO | WO-03095028 A1 | 11/2003 |
| WO | WO-2004011037 A2 | 2/2004 |
| WO | WO-2004012615 A1 | 2/2004 |
| WO | WO-2004026104 A2 | 4/2004 |
| WO | WO-2004032754 A2 | 4/2004 |
| WO | WO-2004032762 A1 | 4/2004 |
| WO | WO-2004032763 A2 | 4/2004 |
| WO | WO-2004037095 A2 | 5/2004 |
| WO | WO-2004060141 A2 | 7/2004 |
| WO | WO-2004078051 A2 | 9/2004 |
| WO | WO-2004098426 A1 | 11/2004 |
| WO | WO-2004112618 A2 | 12/2004 |
| WO | WO-2005052959 A2 | 6/2005 |
| WO | WO-2005117735 A1 | 12/2005 |
| WO | WO-2005122917 A1 | 12/2005 |
| WO | WO-2006012797 A1 | 2/2006 |
| WO | WO-2006021269 A1 | 3/2006 |
| WO | WO-2006036706 A1 | 4/2006 |
| WO | WO-2006042210 A2 | 4/2006 |

(56) References Cited

FOREIGN PATENT DOCUMENTS

| | | |
|---|---|---|
| WO | WO-2006055166 A2 | 5/2006 |
| WO | WO-2006058223 A2 | 6/2006 |
| WO | WO-2006063199 A2 | 6/2006 |
| WO | WO-2006083988 A1 | 8/2006 |
| WO | WO-2006101661 A2 | 9/2006 |
| WO | WO-2006119139 A2 | 11/2006 |
| WO | WO-2006119376 A2 | 11/2006 |
| WO | WO-2006129465 A1 | 12/2006 |
| WO | WO-2007008703 A2 | 1/2007 |
| WO | WO-2007008710 A2 | 1/2007 |
| WO | WO-2007038538 A1 | 4/2007 |
| WO | WO-2007040818 A1 | 4/2007 |
| WO | WO-2007047380 A2 | 4/2007 |
| WO | WO-2007047531 A2 | 4/2007 |
| WO | WO-2007056590 A1 | 5/2007 |
| WO | WO-2007087272 A2 | 8/2007 |
| WO | WO-2007089724 A2 | 8/2007 |
| WO | WO-2007143665 A2 | 12/2007 |
| WO | WO-2008016886 A2 | 2/2008 |
| WO | WO-2008020964 A2 | 2/2008 |
| WO | WO-2008042021 A1 | 4/2008 |
| WO | WO-2008045348 A2 | 4/2008 |
| WO | WO-2008049084 A2 | 4/2008 |
| WO | WO-2008051764 A2 | 5/2008 |
| WO | WO-2008089174 A2 | 7/2008 |
| WO | WO-2008099529 A1 | 8/2008 |
| WO | WO-2008101356 A1 | 8/2008 |
| WO | WO-2008118709 A1 | 10/2008 |
| WO | WO-2008130793 A1 | 10/2008 |
| WO | WO-2009010565 A1 | 1/2009 |
| WO | WO-2009018067 A1 | 2/2009 |
| WO | WO-2009018406 A2 | 2/2009 |
| WO | WO-2009022614 A1 | 2/2009 |
| WO | WO-2009027065 A1 | 3/2009 |
| WO | WO-2009036818 A1 | 3/2009 |
| WO | WO-2009039179 A1 | 3/2009 |
| WO | WO-2009046234 A2 | 4/2009 |
| WO | WO-2009059741 A1 | 5/2009 |
| WO | WO-2009073402 A2 | 6/2009 |
| WO | WO-2009082477 A2 | 7/2009 |
| WO | WO-2009088550 A2 | 7/2009 |
| WO | WO-2009120992 A2 | 10/2009 |
| WO | WO-2009141616 A1 | 11/2009 |
| WO | WO-2009149234 A1 | 12/2009 |
| WO | WO-2010017149 A1 | 2/2010 |
| WO | WO-2010017266 A1 | 2/2010 |
| WO | WO-2010068783 A1 | 6/2010 |
| WO | WO-2010104755 A1 | 9/2010 |
| WO | WO-2011008672 A2 | 1/2011 |
| WO | WO-2011/044338 A2 | 4/2011 |
| WO | WO-2011044343 A2 | 4/2011 |
| WO | WO-2011052939 A2 | 5/2011 |
| WO | WO-2011060031 A1 | 5/2011 |
| WO | WO-2011084768 A1 | 7/2011 |
| WO | WO-2011089717 A1 | 7/2011 |
| WO | WO-2011100321 A2 | 8/2011 |
| WO | WO-2011144911 A1 | 11/2011 |
| WO | WO-2012044597 A1 | 4/2012 |
| WO | WO-2012044606 A2 | 4/2012 |
| WO | WO-2012061638 A1 | 5/2012 |
| WO | WO-2012061722 A2 | 5/2012 |
| WO | WO-2012128362 A1 | 9/2012 |
| WO | WO-2012135705 A1 | 10/2012 |
| WO | WO-2012135721 A1 | 10/2012 |
| WO | WO-2012/150567 A1 | 11/2012 |
| WO | WO-2012166510 A1 | 12/2012 |
| WO | WO-2013018934 A1 | 2/2013 |
| WO | WO-2013034629 A1 | 3/2013 |
| WO | WO-2013062978 A2 | 5/2013 |
| WO | WO-2013102602 A2 | 7/2013 |
| WO | WO-2013154157 A1 | 10/2013 |
| WO | WO-2014092108 A1 | 6/2014 |
| WO | WO-2015197395 A8 | 12/2015 |
| WO | WO-2016009921 A1 | 1/2016 |

OTHER PUBLICATIONS

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomechanical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Chen et al., "Heat-induced changes in the mechanics of a collagenous tissue: pseudoelastic behavior at 37° C.," Journal of Biomechanics, 31, pp. 211-216 (1998).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Wright, et al., "Time-Temperature Equivalence of Heat-Induced Changes in Cells and Proteins," Feb. 1998. ASME Journal of Biomechanical Engineering, vol. 120, pp. 22-26.

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Sullivan, "Optimal Choice for Number of Strands in a Litz-Wire Transformer Winding," IEEE Transactions on Power Electronics, vol. 14, No. 2, Mar. 1999, pp. 283-291.

(56) References Cited

OTHER PUBLICATIONS https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Jang, J. et al. "Neuro-fuzzy and Soft Computing." Prentice Hall, 1997, pp. 13-89, 199-293, 335-393, 453-496, 535-549.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Gooch et al., "Recommended Infection-Control Practices for Dentistry, 1993," Published May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in Medical Infrared Imaging, N. A. Diakides and J. D. Bronzino, Eds. (2008).
Incropera et al., Fundamentals of Heat and Mass Transfer, Wiley, New York (1990). (Book—not attached).
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.

\* cited by examiner

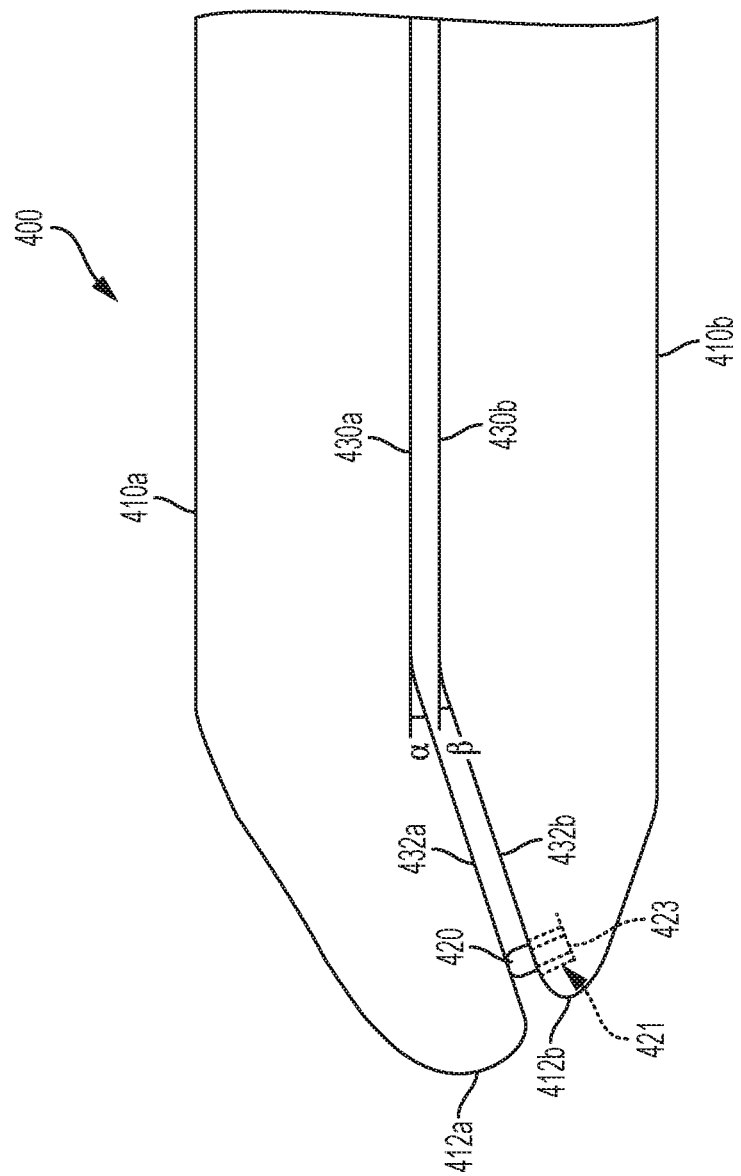

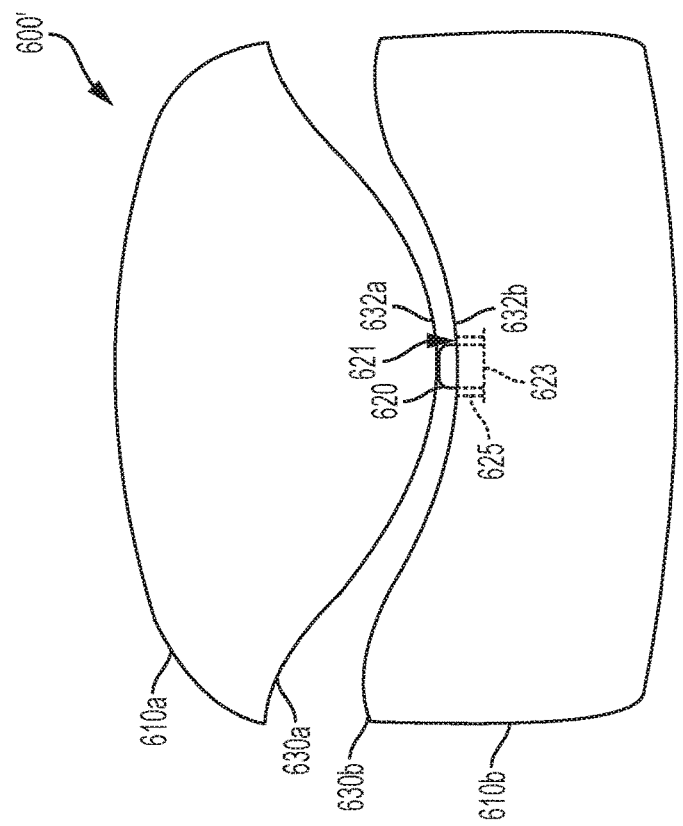
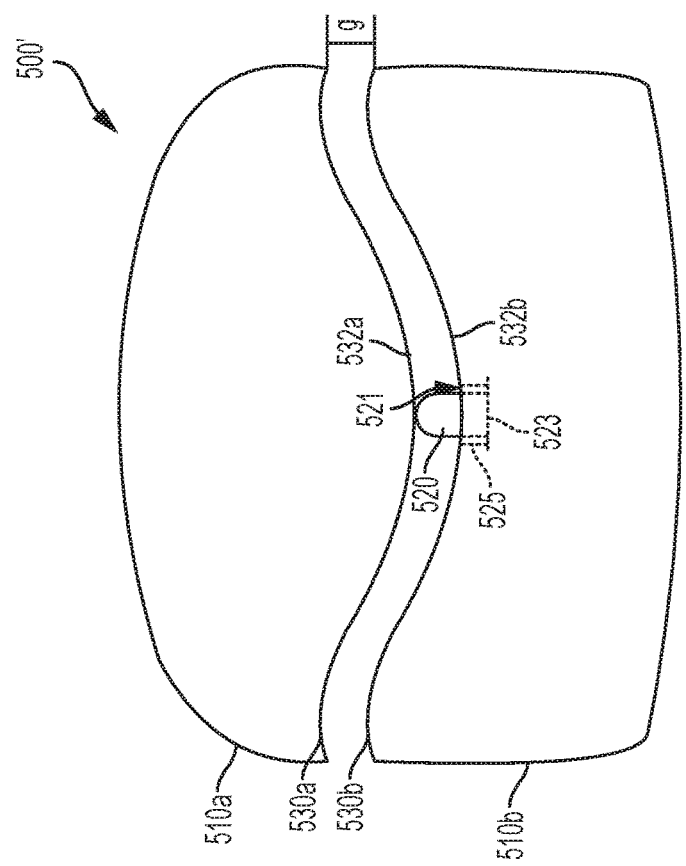

NON-LINEAR JAW GAP FOR ELECTROSURGICAL INSTRUMENTS

RELATED APPLICATIONS

This application is related to the following commonly owned patent applications referenced under:

U.S. patent application Ser. No. 15/142,589 entitled ELECTROSURGICAL INSTRUMENT WITH ELECTRICALLY CONDUCTIVE GAP SETTING MEMBER AND ELECTRICALLY INSULATIVE TISSUE ENGAGING MEMBERS;

U.S. patent application Ser. No. 15/142,598 entitled ELECTROSURGICAL INSTRUMENT WITH CONDUCTIVE GAP SETTING MEMBER AND INSULATIVE TISSUE ENGAGING MEMBER HAVING VARIABLE DIMENSIONS AND STIFFNESS;

U.S. patent application Ser. No. 15/142,609 entitled ELECTROSURGICAL INSTRUMENT WITH ELECTRICALLY CONDUCTIVE GAP SETTING AND TISSUE ENGAGING MEMBERS;

U.S. patent application Ser. No. 15/142,403 entitled JAW STRUCTURE WITH DISTAL POST FOR ELECTROSURGICAL INSTRUMENTS; and U.S. patent application Ser. No. 15/142,446 entitled JAW STRUCTURE WITH DISTAL CLOSURE FOR ELECTROSURGICAL INSTRUMENTS; each of which is incorporated herein by reference in its entirety.

TECHNICAL FIELD

The present disclosure is related generally to medical devices having various mechanisms for grasping and sealing tissue. In particular, the present disclosure is related to medical devices having an electrically conductive gap setting member configured to define a gap between electrodes of an electrosurgical instrument.

BACKGROUND

Electrosurgical devices may be used in many surgical operations. Electrosurgical devices may apply electrical energy to tissue in order to treat tissue. An electrosurgical device may comprise an instrument having a distally mounted end effector comprising one or more electrodes. The end effector can be positioned against tissue such that electrical current may be introduced into the tissue. Electrosurgical devices can be configured for monopolar or bipolar operation. During monopolar operation, current may be introduced into the tissue by an active (or source) electrode on the end effector and returned through a return electrode. The return electrode may be a grounding pad and separately located on a patient's body. During bipolar operation, current may be introduced into and returned from the tissue by the active and return electrodes, respectively, of the end effector.

The end effector may include two or more jaws. At least one of the jaws may have at least one electrode. At least one jaw may be moveable from a position spaced apart from the opposing jaw for receiving tissues to a position in which the space between the jaws is less than that of the first position. This movement of the moveable jaw may compress the tissue held between. Heat generated by the current flow through the tissue in combination with the compression achieved by the jaw's movement may form hemostatic seals within the tissue and/or between tissues and, thus, may be particularly useful for sealing blood vessels, for example.

The end effector may comprise a cutting member. The cutting member may be movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

SUMMARY

In one general aspect, an end effector for an electrosurgical instrument is provided. The end effector includes a first jaw which has a first energy delivery surface, a first distal end, and a first proximal end. The end effector also includes a second jaw having a second energy delivery surface, a second distal end, and a second proximal end. According to various implementations, at least one of the first and second jaws are configured for pivotal movement between at least two positions. The first position is a closed position whereby the first and second distal ends are in proximity and the first and second energy surfaces are facing each other. The second position is an open position whereby the first and second distal ends are separated apart. Further, the first energy delivery surface includes a first, outwardly curved portion and the second energy surface includes a second, inwardly curved portion. The end effector further includes an electrically conductive member that protrudes from either the first or second jaw. The electrically conductive member is in proximity to the first and second distal ends in the closed position.

In yet other another general aspect, the end effector includes an upper jaw which has a first energy delivery surface, a first distal end, and a first proximal end. The end effector also includes a lower jaw which has a second energy delivery surface, a second distal end, and a second proximal end. According to various implementations, the upper and lower jaws are pivotally coupled at the first and second proximal ends. At least one of the upper and lower jaws is configured for pivotal movement between a closed position and an open position. In the closed position, the first and second distal ends are in proximity and the first and second energy sources face each other. In the open position, the first and second distal ends are separated apart. According to additional implementations, the first energy delivery surface has a first angled portion extending to the first distal end, whereby the first angled portion is tilted at a first angle. The second energy surface has a second angled portion extending to the second distal end, whereby the second angled portion is tilted at a second angle. The end effector also includes an electrically conductive member that protrudes from either the first or second jaw. In various embodiments, the electrically conductive member is in proximity to the first and second distal ends in the closed position.

BRIEF DESCRIPTION OF THE FIGURES

The features of the various aspects are set forth with particularity in the appended claims. The various aspects, however, both as to organization and methods of operation, together with advantages thereof, may best be understood by reference to the following description, taken in conjunction with the accompanying drawings as follows:

FIG. 4A shows an elevational view of an end effector with an angled configuration, according to one aspect of the present disclosure.

FIG. 6A shows a front view of an end effector with a laterally curved configuration, according to one aspect of the present disclosure.

FIG. 6B shows front view of an end effector with a laterally curved configuration, according to one aspect of the present disclosure.

DETAILED DESCRIPTION

Figure 1:
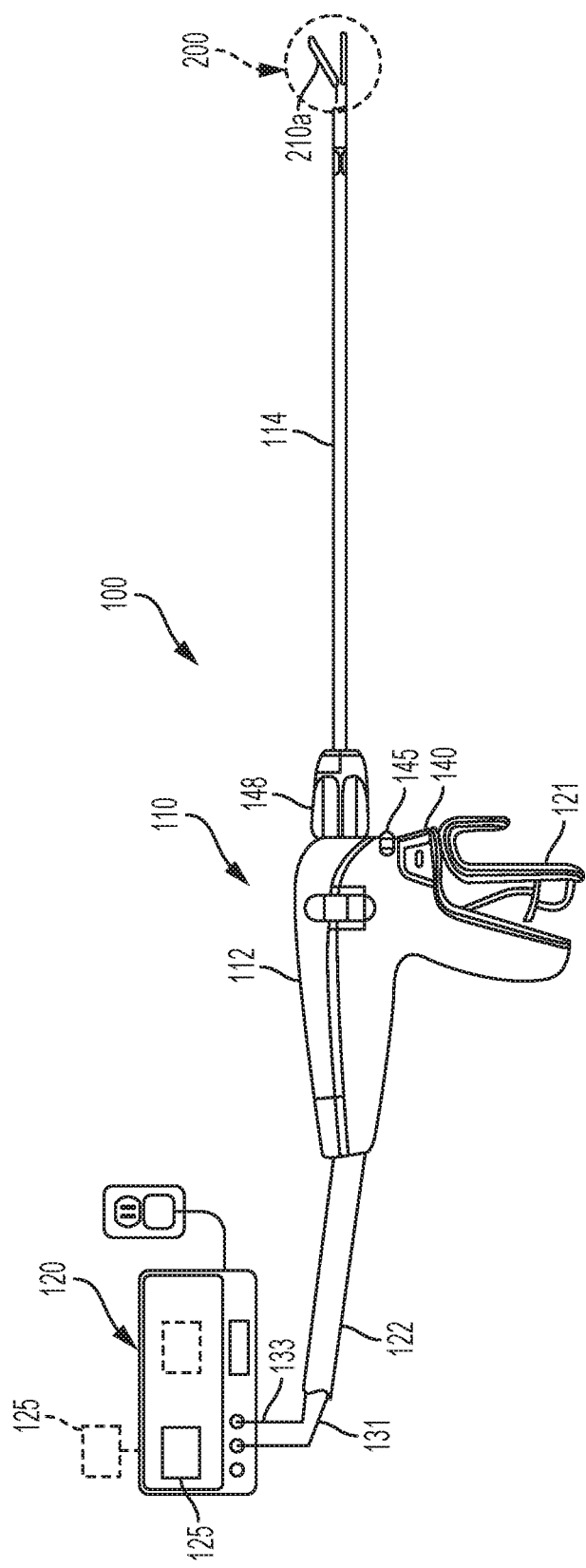
FIG. 1 shows one example of a surgical instrument system, according to one aspect of the present disclosure.

The following description of certain examples of the technology should not be used to limit its scope. Other examples, features, aspects, and advantages of the technology will become apparent to those skilled in the art from the following description, which is, by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, aspects, examples, etc. described herein may be combined with any one or more of the other teachings, expressions, aspects, examples, etc. that are described herein. The following described teachings, expressions, aspects, examples, etc. should, therefore, not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, upper, lower, and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings. Throughout this disclosure, the term "proximal" is used to describe the side of a component, e.g., a shaft, handle assembly, etc., closer to a user operating the surgical instrument, e.g., a surgeon, and the term "distal" is used to describe the side of the component farther from the user operating the surgical instrument.

Aspects of the present disclosure are presented for a single electrosurgical device configured for grasping tissue and performing sealing procedures using electrical and/or other energy. An end effector of the electrosurgical device may include multiple members arranged in various configurations to collectively perform the aforementioned functions. As used herein, an end effector may be referred to as a jaw assembly or clamp jaw assembly comprising an upper jaw member and a lower jaw member where at least one of the upper jaw member and the lower jaw member may be movable relative to the other. Each of the jaw members may be adapted to connect to an electrosurgical energy source. Each jaw member may incorporate an electrode. The electrode may be a positive or negative electrode. In a bipolar electrosurgical device, the electrodes may be adapted for connection to the opposite terminals of the electrosurgical energy source, such as a bipolar radio frequency (RF) generator, so as to generate a current flow therebetween. An electrosurgical energy may be selectively communicated through tissue held between the jaw members to effect a tissue seal and/or treatment. Tissue may be coagulated from the current flowing between the opposite polarity electrodes on each jaw member.

At least one jaw member may include a knife channel defined therein configured to reciprocate a knife there along for severing tissue held between the jaw members. The knife channel may be an extended slot in the jaw member. The knife may be provided within a recess associated with the at least one jaw member. The electrosurgical device may have both coagulation and cutting functions. This may eliminate or reduce instrument interchange during a surgery. Cutting may be achieved using mechanical force alone or a combination of mechanical force and the electrosurgical energy. The electrosurgical energy may be selectively used for coagulation and/or cutting. The knife may be made from an electrically conductive material adapted to connect to the electrosurgical source, and selectively activatable to separate tissue disposed between the jaw members. The knife may be spring biased such that once tissue is severed, the knife may automatically return to an unengaged position within the knife channel or a retracted position in the recess.

In some aspects, the jaw members may be movable relative to each other. During operation of the electrosurgical device, at least one of the jaw members may move from a first, open position where the jaw members can be disposed around a mass of tissue, to a second, closed position where the jaw members grasp the tissue. The jaw members therefore may move through a graspers-like range of motion, similar to that of conventional pliers. In the second position, current flows between the jaw members to achieve hemostasis of the tissue captured therebetween. The jaw members may be configured to have a relatively thick proximal portion to resist bending. At least one of the jaw members may have a three-dimensional configuration with a D-shaped cross-sectional. The three-dimensional configuration with the D-shaped cross-sectional may resist bending. A lock mechanism may be included to lock the jaw members in the closed position. The lock mechanism may set the clamp pressure between the jaw members. At least one electrically conductive gap setting member may be provided between the jaw members to establish a desired gap between electrodes in bipolar electrosurgical devices.

The electrosurgical device may incorporate components to grasp a tissue via the end effector, deliver energy to the tissue via one or more electrodes, and cut the tissue via a dissecting device such as a tissue knife. The structural capabilities of any aspect of an electrosurgical device may be designed for use in one or more of a variety of surgical procedures. In some surgical procedures, the treated tissue may be readily accessible to an end effector affixed to a relatively straight and unbendable shaft. In some alternative surgical procedures, the tissue may not be readily accessible to the end effector on such a shaft. In such procedures, the electrosurgical device may incorporate a shaft designed to bend so that the end effector may contact the tissue requiring treatment. In such a device, the shaft may include one or more articulated joints that may permit the shaft to bend under control by the user. A sliding knife may include a feature to provide actuating force to the sliding knife. A knife actuator may be operably coupled to the shaft for selectively reciprocating the knife through the knife channel.

A front portion assembly may be designed for a specific surgical procedure, while a reusable handle assembly, configured to releasably attach to a front portion assembly, may be designed to provide control of surgical functions common to each front portion assembly, such as tissue grasping, cauterizing, and cutting. Consequently, the number and types of devices required for surgeries can be reduced. The reusable handle assembly may be designed to automate common functions of the electrosurgical device. Device intelligence may be provided by a controller located in the reusable handle assembly that is configured to receive information from a front portion assembly. Such information may include data regarding the type and use of the front portion assembly. Alternatively, information may include data indicative of the position and/or activation of control components (such as buttons or slides that can be manipulated) that may indicate what system functions should be activated and in what manner.

In some non-limiting examples, the controller may supply the RF current when the energy activation control is placed in an activating position by the user. In some alternative non-limiting examples, the controller may supply the RF current for a predetermined period of time once the energy activation control is placed in an activing position. In yet another non-limiting example, the controller may receive data related to the position of the jaws and prevent the RF current from being supplied to the one or more tissue cauterization power contacts if the jaws are not in a closed position.

In some aspects, any of the mentioned examples also may be configured to articulate along at least one axis through various means, including, for example, a series of joints, one or more hinges or flexure bearings, and one or more cam or pulley systems. Other features may include cameras or lights coupled to one or more of the members of the end effector, and various energy options for the surgical device.

The electrosurgical device can be configured to source energy in various forms including, without limitation, electrical energy, monopolar and/or bipolar RF energy, microwave energy, reversible and/or irreversible electroporation energy, and/or ultrasonic energy, heat energy, or any combination thereof, to the tissue of a patient either independently or simultaneously. The energy can be transmitted to the electrosurgical device by a power source in electrical communication with the electrosurgical device. The power source may be a generator. The power source may be connected to the electrosurgical device via a suitable transmission medium such as a cable. The power source may be separate from the electrosurgical device or may be formed integrally with the electrosurgical device to form a unitary electrosurgical system. In one non-limiting example, the power source may include one or more batteries located within a portion of the electrosurgical device. It may be understood that the power source may source energy for use on the tissue of the patient as well as for any other electrical use by other devices, including, without limitation, lights, sensors, communication systems, indicators, and displays, which operate in relation to and/or with the electrosurgical device to form an electrosurgical system.

The electrosurgical device may be configured to source electrical energy in the form of RF energy. The electrosurgical device can transmit the RF energy through tissue compressed between two or more jaws. Such RF energy may cause ionic agitation in the tissue, in effect producing resistive heating, and thereby increasing the temperature of the tissue. Increased temperature of the tissue may lead to tissue cauterization. In some surgical procedures, RF energy may be useful for removing, shrinking, or sculpting soft tissue while simultaneously sealing blood vessels. RF energy may work particularly well on connective tissue, which is primarily composed of collagen and shrinks when contacted by heat. Because a sharp boundary may be created between the affected tissue and the surrounding tissue, surgeons can operate with a high level of precision and control, without sacrificing untargeted adjacent tissue.

The RF energy may be in a frequency range described in EN 60601-2-2:2009+A11:2011, Definition 201.3.218-HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

As discussed above, the electrosurgical device may be used in conjunction with a generator. The generator may be an electrosurgical generator characterized by a fixed internal impedance and fixed operating frequency that deliver maximum power to an external load (e.g., tissue) having an electrical impedance in the range of about 50 ohms to 150 ohms. In this type of bipolar electrosurgical generator, the applied voltage may increase monotonically as the load impedance increases toward the maximum "open circuit" voltage as the load impedance increases to levels of tens of thousands of ohms or more. In addition, the electrosurgical device may be used with a bipolar electrosurgical generator having a fixed operating frequency and an output voltage that may be substantially constant over a range of load impedances of tens of ohms to tens of thousands of ohms including "open circuit" conditions. The electrosurgical device may be advantageously used with a bipolar electrosurgical generator of either a variable voltage design or substantially constant voltage design in which the applied voltage may be interrupted when the delivered current decreases below a predetermined level. Such bipolar generators may be referred to as automatic generators in that they may sense the completion of the coagulation process and terminate the application of voltage, often accompanied by an audible indication in the form of a cessation of a "voltage application" tone or the annunciation of a unique "coagulation complete" tone. Further, the electrosurgical device may be used with an electrosurgical generator whose operating frequency may vary with the load impedance as a means to modulate the applied voltage with changes in load impedance.

Various aspects of electrosurgical devices use therapeutic and/or sub-therapeutic electrical energy to treat tissue. Some aspects may be utilized in robotic applications. Some aspects may be adapted for use in a hand operated manner. In one non-limiting example, an electrosurgical device may include a proximal handle, a distal working end or end effector, and an introducer or elongated shaft disposed in-between.

In some non-limiting medical procedures, the electrosurgical device may be used to weld or seal vessels prior to tissue resection. Such vessels also may be removed as part of procedures to resect other tissue such as cysts, tumors, or infected materials. Blood vessel sealing may reduce bleeding, thereby decreasing potential harmful effects during a resection procedure. In such procedures, vessels may be cut at the cauterization location. It may be understood that complete sealing may be required at the site of the cut to prevent bleeding. It is therefore useful to have an electrosurgical device that may be prevented from cutting a vessel until complete sealing is assured.

To properly seal vessels, two mechanical parameters that affect thickness of the sealed vessel may be accurately controlled: the pressure applied to the vessel and the gap between the electrodes. Proper sealing may require that sufficient pressure is placed on the vessel to assure that the vessel walls are proximate to each other and no intervening gap remains therebetween. The vessel may be compressed to a pressure within a predetermined range. A typical range of appropriate pressures may be between 250 and 1250 pounds per square inch (psi). In addition, proper sealing may require that sufficient power is provided to assure that the vessel walls receive sufficient heat to weld the walls together. Thus, both tissue compression and tissue cauterization may be required to form a proper seal. These can be achieved by the jaw members of the end effector. As mentioned above, the jaw members may grasp, compress, and deliver the energy to the tissue.

To effectively carry out hemostasis, the jaw members should efficiently conduct a proper current flow through the grasped tissue. When that current is insufficient, coagulation of the tissue or vessel may be compromised. When the current is excessive, correspondingly excessive heating may occur with a potential for the generation of damaging electrical arcing. Excessive heating may result in the phenomenon of tissue and blood coagulum sticking to the surface of the jaw members. This may result in increased electrical impedance between the electrodes of the device and the tissue that may subsequently be grasped for the purpose of treatment. Such sticking tissue may evoke a disruption of the coagulated surface, which in itself may compromise the intended hemostatic effect. The end effector may incorporate highly polished electrode surfaces for the purpose of reducing the extent of tissue sticking as well as to facilitate their cleaning when sticking does occur. When grasping tissue, the jaw members may come into mutual contact, causing a short circuit. For example, when a small tissue component is grasped between the jaw members and/or when the jaw members are compressed hard, the electrodes may be in contact with each other in the vicinity of the grasped tissue, causing short-circuiting. The jaw members may include insulative coatings that may be in contact in some geometry, but the insulative coatings may not prevent the short-circuiting.

Arcing may be a possibility as the jaw members closely approach each other. Arcing may happen when monopolar electrosurgical devices are used where the current flows completely through the patient. These high voltage electrical currents may arc from the small electrode to nearby, non-targeted vital structures or may follow erratic paths as they flow through the patient's body, thereby causing damage to tissues both near and at some distance from the electrode. Aberrant current arcs may cause deep tissue necrosis and inadvertent damage to adjacent tissue masses.

Arcing also may happen in a procedure performed by a bipolar electrosurgical device, for example, a "coagulative painting" procedure, where the side surfaces of the electrically active jaw members are drawn over the surface of membranous tissue such as the mesentery. Done properly, this action congeals the microvessels within such thin tissues. However, higher voltage settings on the generator applied across a thin layer of tissue to the other jaw member can cause arcing of the device. For some bipolar electrosurgical devices, microarcs between the electrodes may be normal during operation. However, these microarcs can attack the electrodes. If the electrodes, for example, contain some polymer material, these microarcs can draw out carbon from the polymer material, thus creating carbon tracks, sometimes referred to as "carbon arc tracking," which then may lead to short-circuiting of the electrodes. Also, in general, in case of excessive voltage or sharp edges, a significant arc or a big arc may happen, and the generator may perceive the arc as short-circuiting. Short-circuiting due to either a big arc or carbon arc tracking can be very problematic. This calls for adjustment of the voltage or maintenance of the spacing between the two jaw members to avoid arcing the system. It may be desirable to adjust the spacing rather than changing the applied voltage because lowering the voltage may result in less than desirable tissue effects. Of course, it is also necessary for the surgeon to maintain space between the electrodes of the device to achieve the requisite performance.

In general, for bipolar electrosurgical devices, electrodes of opposite polarity should not contact each other during the application of energy. Shorting of the electrodes effectively shunts energy away from the tissue. Some shunting happens with arcing. It is known that Paschen's Law gives the breakdown voltage, which is the voltage necessary to start a discharge or electric arc between two electrodes in a gas as a function of pressure and gap length. The breakdown voltage of various gases between parallel metal plates as the gas pressure and gap distance were varied has been studied. It has been found that the voltage necessary to arc across the gap decreases as the pressure is reduced and then increases gradually, exceeding its original value. It has also been found that at normal pressure, the voltage needed to cause an arc reduces as the gap size is reduced but only to a point. As the gap is reduced further, the voltage required to cause an arc begins to rise and again exceeds its original value. For a given gas, the voltage is a function only of the product of the pressure and gap length. According to Paschen's Law, at higher pressures and gap lengths, the breakdown voltage is approximately proportional to the product of pressure and gap length. If a bipolar device allows shorting or arcing between the tissue treating electrodes, the effectiveness of the device may be diminished. In one aspect, present disclosure provides an electrically conductive gap setting member to prevent one electrode from contacting the opposed electrode of a bipolar electrosurgical device. In various aspects, the electrically conductive gap setting member may define a uniform or non-uniform gap along the length and/or the width of the jaw member(s) or tissue contacting area thereof.

According to various aspects, an end effector may include an electrically conductive gap setting member to ensure that the electrodes of the jaw members do not electrically contact each other within a range of the closing or opening motion of the jaw members. The electrically conductive gap setting member defines a gap between the upper and lower electrodes of the jaw members when the jaw members are at the closed position. The gap may be uniform or non-uniform along the length and/or width of the tissue contacting area of the jaw. The electrically conductive gap setting member may be dimensioned so that when the jaw members are in the closed position, the gap may be sufficient to prevent electrical shorting between the electrodes. The electrically conductive gap setting member may control the gap distance between opposing electrodes of the jaw members. The heights of the electrically conductive gap setting members are selected as the value to achieve a minimum spacing between the electrode surfaces driving a current path through the grasped tissue, which may be of a distance that does not exceed a value necessary to achieve effective coagulation while avoiding arcing and/or short-circuiting.

In various aspects, the electrically insulative tissue engaging member may comprise an insulating layer. The insulating layer may have a thickness in the range of about 0.002" to about 0.050", more preferably about 0.003" to about 0.007". At thicknesses of about 0.001" or less, the thickness of the insulating layer may be insufficient to prevent shorting of the electrodes. Insulating layer thicknesses above about 0.002" and below about 0.050" may cause adequate hemostasis. It has been observed, however, that the greater the minimum distance between the proximate current conducting portions of the opposing electrodes in the region of current flow through the tissue, the longer the current path through the tissue and the more difficult it may become to obtain the desired localized and intense heating to achieve adequate hemostasis. Insulating layer thicknesses above about 0.050" may be too large for most practical applications using the ceramic insulating materials described.

In various aspects, an electrically conductive gap setting member may be provided between the jaw members. The electrically conductive gap setting member may be affixed on and/or integral to one jaw member and extend to the other jaw member. The electrically conductive gap setting member may protrude through the jaw member. The electrically conductive gap setting member may define a gap between the jaw members. The electrically conductive gap setting member may be electrically conductive. The electrically conductive gap setting member may be a pin. The pin may be metal. The gap setting member can be made of a material that is electrically conductive and also is stiff to resist deformation in response to an applied force. The material is stiff with a high tensile strength and is incompressible. The electrically conductive gap setting member can be made of an electrically conductive metal or metal alloy and preferably can be made of steel, such as medical grade stainless steel, for example. The electrically conductive gap setting member may not contact the electrically conductive surface or portion of any electrode, including the electrode which the electrically conductive gap setting member may be affixed on or protrude through and the opposite electrode. The electrically conductive gap setting member may be sized and configured to avoid short-circuiting between the opposing electrodes and/or ensure that the electrodes would not close enough to arc without the presence of tissue between the electrodes.

In various aspects, the gap between the jaw members or the electrodes may be about 0.002" to about 0.02", preferably about 0.003" to about 0.012", more preferably about 0.004" to about 0.01", even more preferably about 0.004" to about 0.008". The gap between the electrode and the upper of the electrically insulative tissue engaging member on the opposite electrode may be about 0 to about 0.005", preferably about 0.001" to about 0.005", more preferably about 0.001" to about 0.002", more preferably about 0.001". These gaps may be configured to provide desired sealing of vessels. As smaller distances between the electrodes are employed, for example, at values of about 0.001" or about 0.002", arcing may occur. For example, it has been found that as the height diminishes below about 0.005", for example, to about 0.001" or about 0.002", isotonic saline fluid is encountered in the surgical field and the spacing between grasping surfaces, and an arc may form and evoke intense heating in its ionized pathway with resultant damage.

According to various aspects, an end effector may include an electrically insulative member between the jaw members. The electrically insulative member may be provided on at least one of the jaw members. Each jaw member may have a surface. The surface may be a tissue grasping surface. The surface may comprise an electrode. The surface of the upper jaw member may face the surface of the lower jaw member. The electrically insulative member may comprise at least one electrically insulative tissue engaging member. The at least one electrically insulative tissue engaging member is a protuberance in the form of a short cylindrical solid or hollow object, bump, hump, lump, ridge, bulge, knob, swelling peg, or button formed integral with or inserted into a jaw member and protruding through apertures defined by an electrode of the jaw member. The electrically insulative tissue engaging members are configured to facilitate gripping or grasping tissue located between the jaw members and enhance manipulation of tissue during the operation of the electrosurgical device, such as the sealing process.

In some aspects where there may be more than one electrically insulative member, the more than one electrically insulative member may be provided on the same surface or on different surfaces of the jaw members. In some aspects where at least one electrically insulative member may be provided on one surface of a jaw member, effective grasping of very thin tissue and small blood vessels may be provided. Manufacturing costs may be reduced as the at least one electrically insulative member need only be applied to one of the two jaw members. Because it is not required to have the electrically insulative member on both jaw members, it may not be required to precisely control the widths of more than one insulative member and the spacing therebetween to assure required registration between an upper and lower disposed array of electrically insulative members. This may reduce manufacturing costs. This may enhance manufacturability inasmuch as the requirement for precisely registering the insulative members at two grasping surfaces of the jaw members may be eliminated during final assembly.

In various aspects, at least one electrode may be formed on at least one surface of the at least one jaw member. The electrically insulative tissue engaging member may protrude from an aperture in the electrode. In some non-limiting examples, the aperture in the electrode may be line-line same size as the member protruding from the aperture. Therefore, the electrically insulative tissue engaging member may be a tight fit through the aperture. In some other non-limiting examples, the aperture in the electrode may be larger than the electrically insulative tissue engaging member and thereby form a donut around the electrically insulative tissue engaging member. When the aperture is larger than the electrically insulative tissue engaging member, it may be easier for manufacturing since it may be easier to align the electrically insulative tissue engaging members if needed. The aperture may have a diameter twice as large as a diameter of the electrically insulative tissue engaging member. In some aspects, the aperture may have a size such that the space around the electrically insulative tissue engaging member may allow the electrically insulative tissue engaging member to move and/or deform. In any case, the aperture, the electrically insulative tissue engaging member, and the space therebetween should have appropriate sizes and/or dimensions such that the electrosurgical device and its electrodes achieve the requisite performance.

In various aspects, the at least one electrically insulative tissue engaging member may have various shapes. The at least one electrically insulative tissue engaging member may have the shape of a cube, rectangular prism, triangular prism, octagonal prism, tetrahedron, square pyramid, cylinder, cone, sphere, or any other suitable shape. An upper surface of the at least one electrically insulative tissue engaging member may be round, square, rectangle, oval, or any other suitable shape. In some aspects where there is more than one electrically insulative tissue engaging member, the electrically insulative tissue engaging members may each have the same shape or different shapes with any combination of various shapes.

In various aspects, there may be more than one electrically insulative tissue engaging member. The electrically insulative tissue engaging members may have different shapes and/or sizes. All or some of the electrically insulative tissue engaging members may change shapes and/or sizes along the length of the electrodes. The electrically insulative tissue engaging members may have increasing or decreasing sizes along the length of the electrodes. The electrically insulative tissue engaging members may change shapes and/or sizes in a regular fashion or randomly.

In various aspects, the electrodes on the surfaces of the jaw members may be formed of metal. The exposed portions of the surfaces of the jaw members may have smooth surfaces to minimize sticking to tissue or coagulum and to facilitate their cleaning when tissue debris or coagulum does accumulate. The surfaces of the jaw members may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members may include laminar composites of thermally conductive copper and a mechanically stronger material, particularly, higher modulus stainless steel. Biocompatibility of the jaw members may be maintained through an electro-deposited biocompatible metal coating, such as chromium, that coats both the stainless steel and copper laminate while not affecting the electrically insulative tissue engaging members. In some non-limiting examples, for end effectors with small jaw members, for example, having a width of about 0.039" (1 mm) at their tip, laminar composites having a layer of 304 stainless steel of thickness of about 0.011" and a corresponding layer of copper having about 0.052" thickness may be provided. For larger jaw members, laminar composites having a layer of 304 stainless steel of thickness about 0.015" and a corresponding layer of copper having about 0.075" to about 0.085" thickness may be provided. The biocompatible coating may be provided, for example, as an electro-deposited chromium coating, for example, that identified as MEDCOAT 2000™ marketed by Electrolyzing Corporation of Ohio, Cleveland, Ohio 44112. This biocompatible coating is described as meeting or exceeding USP Class VI certification.

The at least one electrically insulative tissue engaging member may be made of electrically insulative material. The electrically insulative material may be alumina, ceramic, nylon, polyphthalamide (PPA), Teflon, polyimide, parylene, any other suitable material, and/or any combinations thereof. In various aspects, smooth metal surfaces may be provided on the surfaces of the jaw members to reduce sticking of tissue or coagulum and these surfaces may be coated with an electrically conductive non-stick coating. Upper surfaces of the at least one electrically insulative tissue engaging member may be coated with electrically insulative non-stick coating material. Such non-stick coating material may be sufficiently thin and/or applied to a sufficiently rough surface to provide a multiplicity of regions on the contacting surfaces that are uncoated with insulative non-stick coating material. Such non-stick coatings may include metal-filled (containing metal particles) organic materials such as fluoropolymers or other compounds generally known under the tradename TEFLON™ (polytetrafluoroethylene polymers and copolymers) or thin fluoropolymers known under the tradename VYDAX™, both of which are manufactured by E.I. DuPont de Nemours of Wilmington, Del. In addition, metallic coatings such as ME-92® (ME-92 Operations, Providence, R.I.) and MEDCOAT 2000™ (supra) may be applied to the stainless steel surfaces of the jaw members to reduce the sticking of tissue thereto.

In various aspects, the length of the jaw members may be set for the particular application in surgery. For example, the length of the jaw members of about 0.4" or 0.5" to about 0.75", such as about 0.47" (12 mm), may be used for smaller anatomical structures or fine work. For larger anatomical structures, the length of the members may be about 1" or greater, for example, about 1.57" (40 mm).

The at least one electrically insulative tissue engaging member may have an appropriate diameter such that the electrically insulative tissue engaging member is neither so small as to pierce tissue nor so large as to take away too much of the electrode surface. The minimum diameter of the member may be about 0.03125" (1/32") as an electrically insulative tissue engaging member of this diameter may not pierce tissue unless the pressure applied on the tissue from the electrically insulative tissue engaging member is very high. If too much of the electrode surface is taken away by the electrically insulative tissue engaging member or members, there may be too little of the electrode surface and therefore, too little of the electrically conductive area adjacent to the electrically insulative tissue engaging member/members, and the electrosurgical device and/or the electrodes may not achieve the requisite performance. In some aspects where there is more than one electrically insulative tissue engaging member, the electrically insulative tissue engaging members may have the same or different diameters of any combination.

The at least one electrically insulative tissue engaging member may have a height about 0.001" smaller than the gap between the electrodes or jaw members, for example, about 0.001" to about 0.019", preferably about 0.002" to about 0.011", more preferably about 0.003" to about 0.009", such as about 0.008", about 0.003" to about 0.007", or about 0.004" to about 0.007". In general, the height may be less than about 0.020" or less than or equal to about 0.010". The minimum value found practical for the height may be about 0.003". In some aspects where there is more than one electrically insulative member, the members may have the same or different heights of any combination.

These sizes may be selected to achieve the most efficient electrode contact geometry for achieving the most efficient hemostasis with respect to tissue or vessels grasped. The sizes and/or dimensions may be configured such that the electrosurgical device and the electrodes achieve the requisite performance.

In various aspects, the electrically insulative tissue engaging members may have the same height or different heights. The members may be provided on one jaw member and received in receiving pockets on the other jaw member. The depths of the receiving pockets may vary. The electrically insulative members and the receiving pockets may be configured to define a non-uniform arrangement along the length of the jaw members.

In various aspects, the electrically insulative tissue engaging members may be integrally formed in the electrode. The electrically insulative tissue engaging members may be molded in the electrode(s). The electrically insulative tissue engaging members may be fabricated by an insert molding manufacturing process. This may reduce the cost of manufacturing. In some other aspects, the electrically insulative tissue engaging members may be inserted into openings defined in the electrode(s). In some other aspects, the electrode on the surface of one jaw member may be coined or bent to form tissue grasping members having the same function as the electrically insulative tissue engaging members that may contact a non-electrically conductive portion on the surface of the other jaw member. Portions on the surface of the other jaw member corresponding to the electrically insulative tissue engaging members may be cut out to expose the non-electrically conductive portion and receive the electrically insulative tissue engaging members. In some other aspects, the electrically insulative tissue engaging members may be formed on an embossed insert that may be inserted in an insulated material in one jaw member. The embossed insert may be inserted and set in glue in the jaw member. A shim may be used to set the heights of the electrically insulative tissue engaging members.

In various aspects, the electrically insulative tissue engaging members may be formed of ceramic, glass, or glass/ceramic applied by plasma deposition methods; physical vapor deposition; screen or pad printing followed by fusing of the insulative layer by exposure to high temperatures; a photolithography process; or attachment of individual ceramic members using brazing, soldering, or adhesive bonding methods. The electrically insulative tissue engaging members may be formed from plastic and using coating methods such as, for example, dipping, plasma coating, encasement, or the like.

In some non-limiting examples, the electrically insulative tissue engaging members may be provided as discrete, spaced-apart members disposed in arrays on one surface of a jaw member. The electrically insulative tissue engaging members may be cubes or any other suitable shapes. The electrically insulative tissue engaging members defined within the arrays may be formed by first depositing, for example, by plasma deposition or physical vapor deposition, an electrically insulative layer over a desired length of the surface. Next, thin grinding wheels can be used to grind away the electrically insulative layer to produce the pattern of electrically insulative tissue engaging members. In some non-limiting examples, the electrically insulative tissue engaging members or arrays may be formed by thick film printing of insulative material followed by exposure to elevated temperatures to affect its bonding to the surface. In some non-limiting examples, the electrically insulative tissue engaging members may be formed as layers utilizing a physical mask to deposit the electrically insulative material in required areas on the surface. Alternatively, the surface may be configured containing an array of apertures of circular cross-sectional, peripheral shape, or any other suitable shape. The electrically insulative tissue engaging members may then be provided as electrically insulative glass, ceramic, or glass/ceramic pegs inserted within the apertures.

In the following detailed description, reference is made to the accompanying drawings, which form a part hereof. In the drawings, similar symbols and reference characters typically identify similar components throughout the several views, unless context dictates otherwise.

In various embodiments, there may be more than one electrically insulative tissue engaging member. The tissue engaging members may have different shapes and/or sizes. All or some of the tissue engaging members may change shapes and/or sizes along the length of the electrodes. The tissue engaging members may have increasing or decreasing sizes along the length of the electrodes. The tissue engaging members may change shapes and/or sizes in a regular fashion or randomly.

In various embodiments, the electrodes on the surfaces of the jaw members may be formed of metal. The exposed portions of the surfaces of the jaw members may have smooth surfaces to minimize sticking to tissue or coagulum and to facilitate their cleaning when tissue debris or coagulum does accumulate. The surfaces of the jaw members may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members may include laminar composites of thermally conductive copper and a mechanically stronger material, particularly, higher modulus stainless steel. Biocompatibility of the jaw members may be maintained through an electro-deposited biocompatible metal coating, such as chromium, that coats both the stainless steel and copper laminate while not affecting the tissue engaging members. In some non-limiting examples, for end effectors with small jaw members, for example, having a width of about 1 mm at their tip, laminar composites having a layer of 304 stainless steel of thickness of about 11 mils and a corresponding layer of copper having about at 52 mils thickness may be provided. For larger jaw members, laminar composites having a layer of 304 stainless steel of thickness about 15 mils and a corresponding layer of copper having about 75 to 85 mils thickness may be provided. The biocompatible coating may be provided, for example, as an electro-deposited chromium coating, for example, that identified as MEDCOAT 2000™ marketed by Electrolyzing Corporation of Ohio, Cleveland, Ohio 44112. This biocompatible coating is described as meeting or exceeding USP Class VI certification.

The at least one electrically insulative tissue engaging member may be made of electrically insulative material. The electrically insulative material may be alumina, ceramic, nylon, Teflon, polyimide, parylene, any other suitable material, and/or any combinations thereof. In various embodiments, smooth metal surfaces may be provided on the surfaces of the jaw members to reduce sticking of tissue or coagulum and these surfaces may be coated with an electrically conductive non-stick coating. Top surfaces of the at least one tissue engaging member may be coated with electrically insulative non-stick coating material. Such non-stick coating material may be sufficiently thin and/or applied to a sufficiently rough surface to provide a multiplicity of regions on the contacting surfaces that are uncoated with insulative non-stick coating material. Such non-stick coatings may include metal-filled (containing metal particles) organic materials such as fluoropolymers or other compounds generally defined as Teflon™ (polytetrafluoroethylene polymers and copolymers) or thin fluoropolymers such as Vydax™, both of which are manufactured by E.I. DuPont de Nemours of Wilmington, Del. In addition, metallic coatings such as ME-92 (ME-92 Operations, Providence, R.I.) and MEDCOAT 2000™ (supra) may be applied to the stainless steel surfaces of the jaw members to reduce the sticking of tissue thereto.

In one embodiment, the length of the jaw members may preferably be 15-25 millimeters (0.59-0.98 inches), for example for a laparoscopic instrument. In another embodiment, the length of the jaw members may preferably be 30-45 millimeters (1.18-1.77 inches), for example for an open procedure device.

In various embodiments, the uniform or non-uniform gap between the jaw members may be 0.002-0.012 inches, preferably 0.003-0.008 inches.

The at least one electrically insulative tissue engaging member may have a diameter of 0.015-0.045 inches, preferably about 0.02 inches. In some aspects where there is more than one tissue engaging member, the tissue engaging members may have the same or different diameters of any combination.

The at least one electrically insulative tissue engaging member may have a height of 0.002-0.012 inches, preferably 0.003-0.008 inches, more preferably 0.003-0.004 inches. In some aspects where there is more than one electrically insulative tissue engaging member, the tissue engaging members may have the same or different heights of any combination. As smaller spacings are employed, for example, at values of about 0.001" or 0.002", arcing may occur. For example, it has been found that as the height diminishes below about 0.005", for example, to 0.001" or 0.002", isotonic saline fluid is encountered in the surgical field and the spacing between grasping surfaces, and an arc may form and evoke intense heating in its ionized pathway with resultant damage.

These sizes may be selected to achieve the most efficient electrode contact geometry for achieving the most efficient hemostasis with respect to tissue or vessels grasped.

In various embodiments, the electrically insulative tissue engaging members may have the same height or different heights. The tissue engaging members may be provided on one jaw member and received in receiving pockets on the other jaw member. The depths of the receiving pockets may vary. The electrically insulative tissue engaging members and the receiving pockets may be configured to form a nonuniform gap between the jaw members.

In various embodiments, a gap setting member may be provided between the jaw members. The gap setting member may be affixed on one jaw member and extend above the sealing surface of the jaw member. The gap setting member may define a gap between the jaw members by itself or with the electrically insulative tissue engaging members. The gap setting member may be conductive or insulative. The gap setting member may be a pin. The gap setting member may or may not touch the electrodes. The gap setting member may be configured such that the opposing electrodes may not be conductively connected to each other in any way to avoid short-circuiting.

In various embodiments, the electrically insulative tissue engaging members may be integrally formed in the electrode. The tissue engaging members may be molded in the electrode. The tissue engaging members may be fabricated by an insert molding manufacturing process. This may reduce the cost of manufacturing. In some other embodiments, the tissue engaging members may be inserted into openings in the electrode. In some other embodiments, the electrode on the surface of one jaw member may be coined or bent to form the electrically insulative tissue engaging members that may contact a nonconductive portion of the other jaw member's surface. Portions on the surface of the other jaw member corresponding to the tissue engaging members may be cut out to expose the nonconductive portion and receive the electrically insulative tissue engaging members. In some other embodiments, the tissue engaging members may be formed on a stamped insert that may be inserted in an insulated material in one jaw member. The stamped insert may be inserted and set in glue in the jaw member. A shim may be used to set the heights of the tissue engaging members.

In various embodiments, the electrically insulative tissue engaging member may be formed of ceramic, glass, or glass/ceramic applied by plasma deposition methods; physical vapor deposition; screen or pad printing followed by fusing of the insulative layer by exposure to high temperatures; a photolithography process; or attachment of individual ceramic members using brazing, soldering, or adhesive bonding methods. The tissue engaging members may be formed from plastic and using coating methods such as, for example, dipping, plasma coating, encasement, or the like.

In some non-limiting examples, the electrically insulative tissue engaging members may be provided as discrete, spaced-apart members disposed in arrays on one surface of a jaw member. The tissue engaging members may be cubes or any other suitable shapes. The electrically insulative tissue engaging member defined within the arrays may be formed by first depositing, for example, by plasma deposition or physical vapor deposition, an electrically insulative layer over a desired length of the surface. Next, thin grinding wheels can be used to grind away the electrically insulative layer to produce the pattern of electrically insulative tissue engaging members. The heights of the members as they protrude from the surface should establish the distance or spacing discussed above. In some non-limiting examples, the electrically insulative tissue engaging member or arrays may be formed by thick film printing of insulative material followed by exposure to elevated temperatures to effect its bonding to the surface. In some non-limiting examples, the electrically insulative tissue engaging members may be formed as layers utilizing a physical mask to deposit the electrically insulative material in required areas on the surface. Alternatively, the surface may be configured containing an array of holes of circular cross-sectional, peripheral shape, or any other suitable shape. The spacers may then be provided as electrically insulative glass, ceramic, or glass/ceramic pegs inserted within the holes.

Reference will now be made in detail to several aspects, including example implementations of an end effector for electrosurgical instruments. Wherever practicable similar or like reference numbers may be used in the figures and may indicate similar or like functionality. The figures depict examples of the disclosed surgical instruments and/or methods of use for purposes of illustration only. One skilled in the art will readily recognize from the following description that alternative examples of the structures and methods illustrated herein may be employed without departing from the principles described herein.

An end effector for an electrosurgical instrument is frequently used to grasp bleeding thin fragile tissues. Thus precise and effective acquisition, retention and sealing of such tissues are desired. Furthermore, electrodes of opposite polarity of the end effector should not contact each other. Shorting the electrodes effectively shunts energy away from the tissue. Additionally, it is important for the two jaws of an end effector to align to each other while in a closed configuration. Otherwise a tissue-cutting element of the electrosurgical instrument may create unwanted damages.

Various aspects of an improved end effector for an electrosurgical instrument are disclosed, which improves grasping of tissues, avoids shorting the electrodes, and/or improves alignment of jaws. Aspects of the present disclosure may be used with, for example, a laparoscopy vessel sealer.

FIG. 1 shows one example of a surgical instrument system 100, according to one aspect of the present disclosure. The surgical instrument system 100 comprises an electrosurgical instrument 110. The electrosurgical instrument 110 may comprise a proximal handle 112, a distal working end or end effector 200 and an introducer or elongated shaft 114 disposed in-between. Alternatively, the end effector may be attached directly to the handle as in scissor style devices such as the electrosurgical instrument described in U.S. Pat. No. 7,582,087.

The electrosurgical system 100 can be configured to supply energy, such as electrical energy, ultrasonic energy, heat energy, or any combination thereof, to the tissue of a patient either independently or simultaneously, for example. In one example, the electrosurgical system 100 may include a generator 120 in electrical communication with the electrosurgical instrument 110. The generator 120 may be connected to the electrosurgical instrument 110 via a suitable transmission medium such as a cable 122. In one example, the generator 120 may be coupled to a controller, such as a control unit 125, for example. In various aspects, the control unit 125 may be formed integrally with the generator 120 or may be provided as a separate circuit module or device electrically coupled to the generator 120 (shown in phantom to illustrate this option). The control unit 125 may include automated or manually operated controls to control the amount of current delivered by the generator 120 to the electrosurgical instrument 110. Although as presently disclosed, the generator 120 is shown separate from the electrosurgical instrument 110, in some aspects, the generator 120 (and/or the control unit 125) may be formed integrally with the electrosurgical instrument 110 to form a unitary electrosurgical system 100, where a battery located within the electrosurgical instrument 110 may be the energy source and a circuit coupled to the battery produces the suitable electrical energy, ultrasonic energy, or heat energy.

In one aspect, the generator 120 may comprise an input device located on a front panel of the generator 120 console. The input device may comprise any suitable device that generates signals suitable for programming the operation of the generator 120, such as a keyboard, or input port, for example. In one example, one or more electrodes in the first jaw 210a and one or more electrodes in the second jaw 210b may be coupled to the generator 120. The cable 122 may comprise multiple electrical conductors for the application of electrical energy to a first electrode (which may be designated as a + electrode) and to a second electrode (which may be designated as a − electrode) of the electrosurgical instrument 110. It may be recognized that + and − designations are made solely for convenience and do not indicate an electrical polarity. An end of each of the conductors may be placed in electrical communication with a terminal of the generator 120. The generator 120 may have multiple terminals, each configured to contact one or more of the conductors. The control unit 125 may be used to activate the generator 120, which may serve as an electrical source. In various aspects, the generator 120 may comprise an RF source, an ultrasonic source, a direct current source, and/or any other suitable type of electrical energy source, for example, which may be activated independently or simultaneously.

In various aspects, the electrosurgical system 100 may comprise at least one supply conductor 131 and at least one return conductor 133, wherein current can be supplied to the electrosurgical instrument 110 via the at least one supply conductor 131 and wherein the current can flow back to the generator 120 via the at least one return conductor 133. In various aspects, the at least one supply conductor 131 and the at least one return conductor 133 may comprise insulated wires and/or any other suitable type of conductor. As described below, the at least one supply conductor 131 and the at least one return conductor 133 may be contained within and/or may comprise the cable 122 extending between, or at least partially between, the generator 120 and the end effector 200 of the electrosurgical instrument 110. The generator 120 can be configured to apply a sufficient voltage differential between the supply conductor 131 and the return conductor 133 such that sufficient current can be supplied to the end effector 200 to perform the intended electrosurgical operation.

The shaft 114 may have a cylindrical or rectangular cross-section, for example, and can comprise a thin-wall tubular sleeve that extends from the proximal handle 112. The shaft 114 may include a bore extending therethrough for carrying actuator mechanisms, for example, an axially moveable member for actuating the jaws 210a, 210b and for carrying electrical leads for delivery of electrical energy to electrosurgical components of the end effector 200. The proximal handle 112 may include a jaw closure trigger 121 configured to adjust the position of the jaws 210a, 210b with respect to each other. In one non-limiting example, the jaw closure trigger 121 may be coupled to an axially moveable member disposed within the shaft 114 by a shuttle operably engaged to an extension of the jaw closure trigger 121.

The end effector 200 may be adapted for capturing and transecting tissue and for contemporaneously welding the captured tissue with controlled application of energy (e.g., RF energy). The first jaw 210a and the second jaw 210b may be closed thereby capturing or engaging tissue. The first jaw 210a and second jaw 210b also may apply compression to the tissue. In some aspects, the shaft 114, along with the first jaw 210a and second jaw 210b, can be rotated, for example, a full 360°. For example, a rotation knob 148 may be rotatable about the longitudinal axis of the shaft 114 and may be coupled to the shaft 114 such that rotation of the knob 148 causes corresponding rotation of the shaft 114. The first jaw 210a and the second jaw 210b can remain openable and/or closeable while rotated.

Also illustrated in FIG. 1 are a knife advancement control 140 and an energy activation control 145 located on the proximal handle 112. In some non-limiting examples, the knife advancement control 140 and the energy activation control 145 may be depressible buttons positioned to permit a user to control knife advancement or energy activation by the use of one or more fingers.

Figure 2:
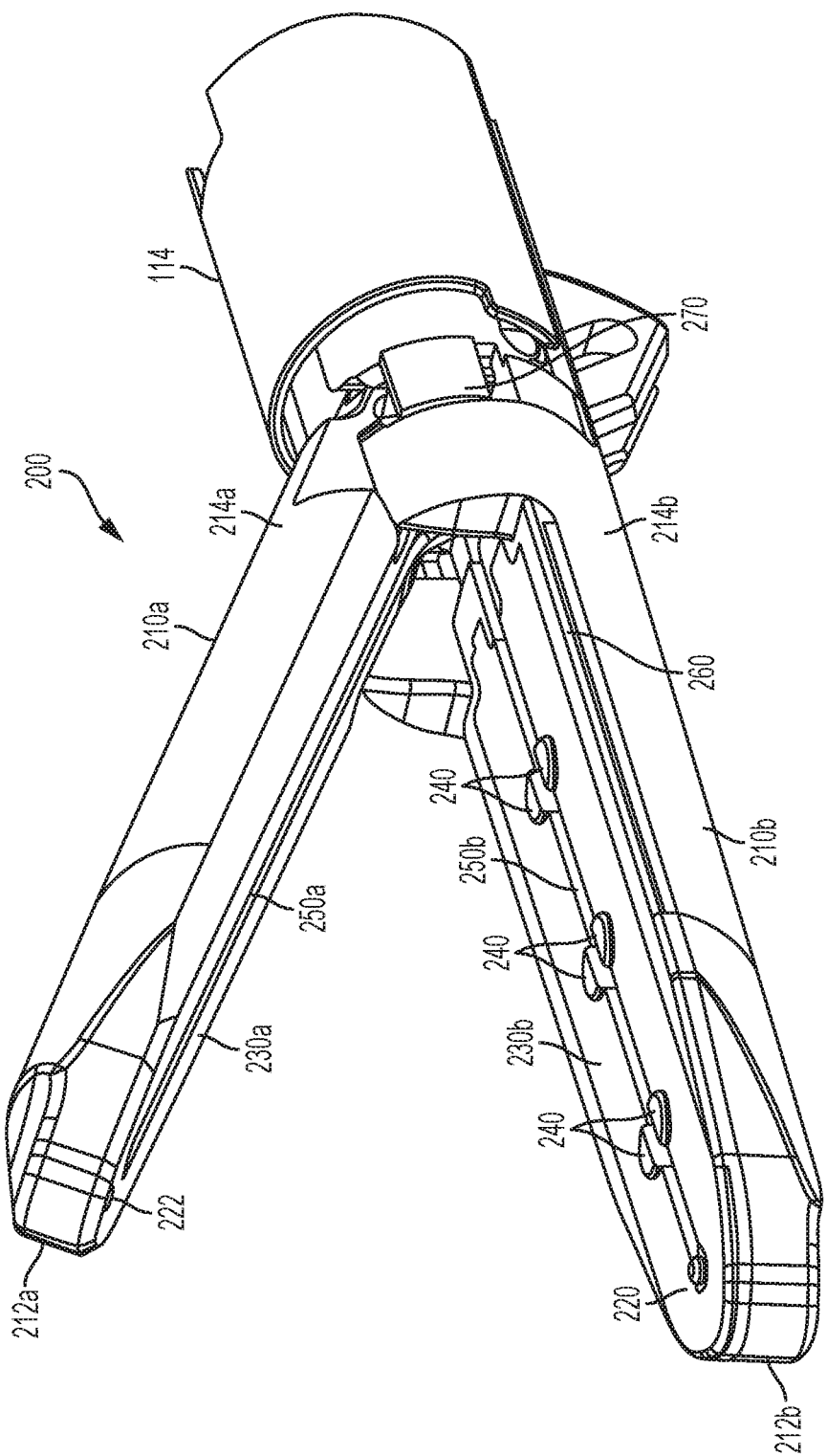
FIG. 2 shows a perspective view of an end effector with jaws open, according to one aspect of the present disclosure.

FIG. 2 shows a perspective view of the end effector 200 with the jaws 210a, 210b open, according to one aspect of the present disclosure. The end effector 200 may comprise the first or upper jaw 210a and the second or lower jaw 210b, which may be straight or curved. The upper jaw 210a may comprise a first distal end 212a and a first proximal end 214a. The lower jaw 210b may comprise a second distal end 212b and a second proximal end 214b. The first distal end 212a and the second distal end 212b may be collectively referred to as the distal end of the end effector when the jaws 210a, 210b are in a closed configuration. The first proximal end 214a and the second proximal end 214b may be collectively referred to as the proximal end of the end effector 200. The jaws 210a, 210b are pivotally coupled at the first and second proximal ends 214a, 214b. As shown in FIG. 2, The lower jaw 210b is fixed and the upper jaw 210a is pivotally movable relative to the lower jaw 210b from an open position to a closed position and vice versa. In the closed position, the first and second distal ends 212a, 212b are in proximity. In the open position, the first and second distal ends 212a, 212b are spaced apart. In other aspects, the upper jaw 210a may be fixed and the lower jaw 210b may be movable. In other aspects, both the upper and lower jaws 210a, 210b may be movable. The end effector 200 may comprise a pivot assembly 270 located at or in proximity to the proximal end of the end effector, which sets an initial gap between the jaws 210a, 210b at the proximal end of the end effector 200 in a closed position. The pivot assembly 270 may be welded in place in a gap setting process during manufacturing of the end effector 200, as described in greater detail below.

The first jaw 210a and the second jaw 210b may each comprise an elongated slot or channel 250a and 250b, respectively, disposed along their respective middle portions. The channels 250a and 250b may be sized and configured to accommodate the movement of an axially moveable member (not shown), which may comprise a tissue-cutting element, for example, comprising a sharp distal edge. The upper jaw 210a may comprise a first energy delivery surface 230a. The lower jaw 210b may comprise a second energy delivery surface 230b. The first and second energy delivery surfaces 230a, 230b face each other when the jaws 210a, 210b are in a closed configuration. The first energy delivery surface 230a may extend in a "U" shape around the channel 250a, connecting at the first distal end 212a. The second energy delivery surface 230b may extend in a "U" shape around the channel 250b, connecting at the second distal end 212b. The first and second energy delivery surfaces 230a, 230b may comprise electrically conductive material such as copper, gold plated copper, silver, platinum, stainless steel, aluminum, or any suitable electrically conductive biocompatible material, for example. The second energy delivery surface 230b may be connected to the supply conductor 131 shown in FIG. 1, thus forming the first electrode of the electrosurgical instrument 110. The first energy delivery surface 230a may be connected and the return conductor 133 shown in FIG. 1, thus forming the second electrode of the electrosurgical instrument 110. For example, the first energy delivery surface 230a may be grounded. Opposite connection is also possible.

As shown in FIG. 2, the second energy delivery surface 230b is formed by a conductive layer disposed, or at least partially disposed, along at least a portion of the body of the lower jaw 210b. The electrically conductive layer comprising the second energy delivery surface 230b may extend to the second distal end 212b, and thus operation of the end effector 200 is possible without actually grasping the tissue. The lower jaw 210b may further comprise an electrically insulative layer 260 arranged between the conductive layer and the body of the lower jaw 210b. The electrically insulative layer 260 may comprise electrically insulative material such as ceramic or nylon. Furthermore, the first energy delivery surface 230a is formed of an electrically conductive layer disposed, or at least partially disposed, along at least a portion of the body of the upper jaw 210a. The upper jaw 210a also may comprise an electrically insulative layer arranged between the conductive layer and the body of the upper jaw 210a.

The upper and lower jaws 210a and 210b may each comprise one or more electrically insulative tissue engaging members arranged on the first or second energy delivery surface 230a, 230b, respectively. Each of the electrically insulative tissue engaging members may protrude from the energy delivery surface and define a height above the energy delivery surface, and thus is sometimes referred to as a "tooth". The electrically insulative tissue engaging members may comprise electrically insulative material such as ceramic or nylon. As shown in FIG. 2, the electrically insulative tissue engaging members 240 are arranged longitudinally, i.e., along the length of the lower jaw 210b, from the second proximal end 214b to the second distal end 212b and on the second energy delivery surface 230b. As shown in FIG. 2, the electrically insulative tissue engaging members 240 are in pairs, and each pair is arranged next to the channel 250b and is separated by the channel 250b. These paired electrically insulative tissue engaging members 240 as arranged here are sometimes referred to as "teeth".

In other aspects, other configurations of the electrically insulative tissue engaging members 240 are possible. For example, the electrically insulative tissue engaging members 240 may be located at a distance away from the channel. For example, the electrically insulative tissue engaging members 240 may be arranged in a grid on the energy delivery surface. In other aspects, the electrically insulative tissue engaging members 240 may not have the half cylindrical cross sections as shown in FIG. 2, and may have cylindrical cross sections or rectangular cross sections. In other aspects, electrically insulative tissue engaging members 240 may be arranged on the first energy delivery surface 230a, or may be arranged on both of the first and second energy delivery surfaces 230a, 230b.

The lower jaw 210b further comprises a distal electrically conductive gap setting member 220 in proximity to the second distal end 212b. The electrically conductive gap setting member 220 is located in proximity to the edge of the second energy delivery surface 230b at the second distal end 212b. The electrically conductive gap setting member 220 also may be located at a distance away from the lateral edges of the second energy delivery surface 230b. The electrically conductive gap setting member 220 protrudes from the lower jaw 210b and defines a height above the second energy delivery surface 230b. The electrically conductive gap setting member 220 may be substantially in a shape of a post or a cylinder, or any other shape that protrudes from the lower jaw 210b. The tip (outward end) of the electrically conductive gap setting member 220 may be rounded. The electrically conductive gap setting member 220 comprises an electrically conductive material such as stainless steel. The electrically conductive gap setting member 220 extends beyond the conductive layer and the insulative layer 260 and is connected to the body of the second jaw 210b, which is connected to the ground. Because the upper jaw 210a is also connected to the ground, the electrically conductive gap setting member 220 has a same polarity with the upper jaw 210a. The electrically conductive gap setting member 220 is arranged so that it is not in contact with the conductive layer (conductive material) of the second energy delivery surface 230b, or in other words, electrically isolated from the conductive material of the second energy delivery surface 230b. For example, the electrically conductive gap setting member 220 may be located near the bottom of the "U" shaped conductive layer on the lower jaw 210b but is separated from the conductive layer. Optionally, the upper jaw 210b may further comprise a recession 222 at or in proximity to the first distal end 212a. The recession 222 may be adapted to receive the electrically conductive gap setting member 220 when the jaws 210a, 210b are in a closed configuration. Therefore, the alignment between the jaws 210a, 210b when they are in a closed configuration may be improved.

In other aspects, the electrically conductive gap setting member 220 may be arranged on the upper jaw 210a, and the recession 222 may be arranged on the lower jaw 210b. In other aspects, the upper jaw 210a and the lower jaw 210b may each comprise an electrically conductive gap setting member. In other aspects, the upper jaw 210a and/or the lower jaw 210b may each comprise more than one electrically conductive gap setting member. In certain aspects, the electrically conductive gap setting member 220 and the electrically insulative tissue engaging members 240 may not be on a same jaw.

Figure 3A:
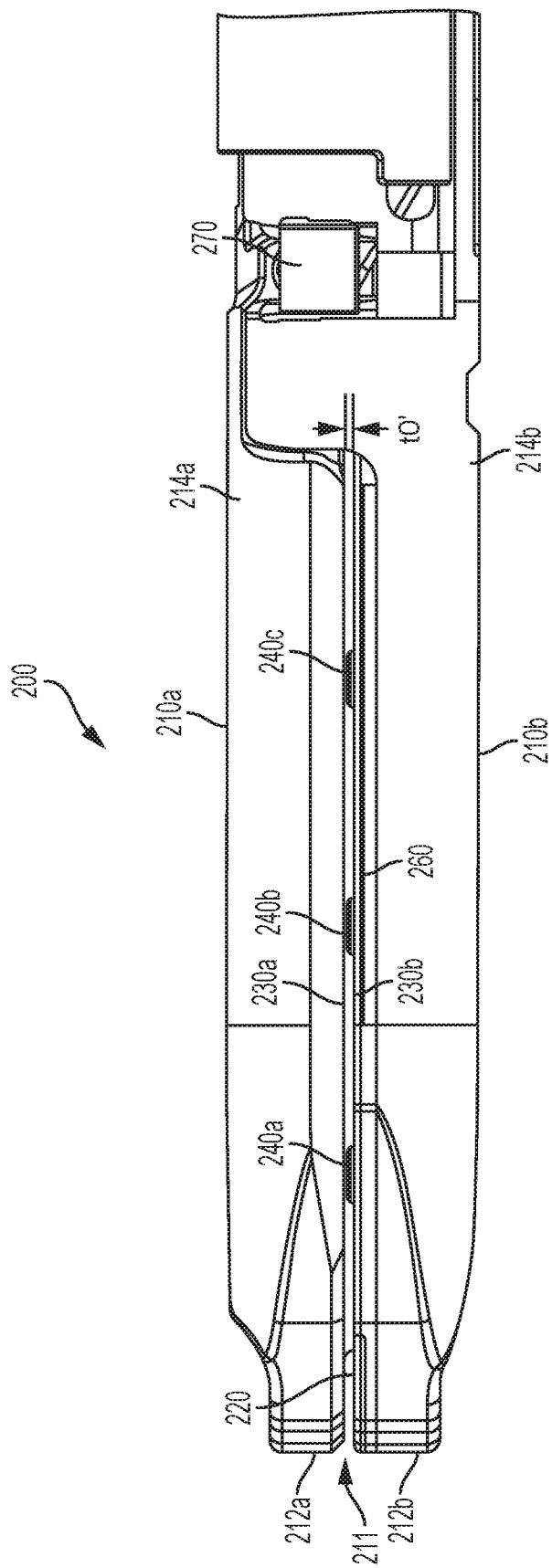
FIG. 3A shows an elevational view of the end effector with the jaws closed, according to one aspect of the present disclosure.

FIG. 3A shows an elevational view of the end effector 200 with the jaws 210a, 210b closed, according to one aspect of the present disclosure. In the closed position shown by FIG. 3A, the upper jaw 210a and the lower jaw 210b define a gap 211 between the first energy delivery surface 230a and the second energy delivery surface 230b in the closed position. In various aspects, the gap 211 defines a minimum distance between the first energy delivery surface 230a and the second energy delivery surface 230b. In at least one instance, the gap 211 is a uniform gap, and a uniform minimum distance is maintained between the first energy delivery surface 230a and the second energy delivery surface 230b along the length of the first energy delivery surface 230a and/or the second energy delivery surface 230b.

Alternatively, the gap 211 can be a non-uniform gap. A first minimum distance can be defined between the first energy delivery surface 230a and the second energy delivery surface 230b at a first position in proximity to the distal ends 212a and 212b while a second minimum distance different from the first minimum distance can be defined between the first energy delivery surface 230a and the second energy delivery surface 230b at a second position in proximity to the proximal ends 214a and 214b, for example.

In various instances, a minimum distance between the first energy delivery surface 230a and the second energy delivery surface 230b is equal from about 0.0005" (about 13 µm) to about 0.040" (about 1 mm), for example, and in some aspects, between about 0.001" (about 25 µm) to about 0.010" (about 250 µm), for example. In some non-limiting examples, a minimum distance may have values of about 0.0005" (about 13 µm), about 0.001" (about 25 µm), about 0.002" (about 51 µm), about 0.004" (about 100 µm), about 0.005" (about 130 µm), about 0.01" (about 250 µm), about 0.02" (about 510 µm), about 0.04" (about 1 mm), or a range between any two of these values including endpoints.

When the jaws 210a, 210b are closed or nearly closed, they may grasp a tissue in between and contact opposite sides of the tissue, and current supplied by the generator 120 may pass along the supply conductor 131 to the lower jaw 210b and the second energy delivery surface 230b, through the tissue, and then return via the first energy delivery surface 230a, the upper jaw 210a, and the return conductor 133 to the generator 120. In this manner, the tissue between the upper jaw 210a and the lower jaw 210b forms a load for the generator 120.

Figure 3C:
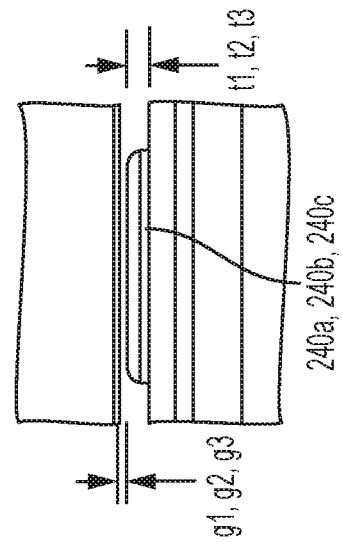
FIG. 3C shows an enlarged view of electrically insulative tissue engaging members according to one aspect of the present disclosure.
Figure 3B:
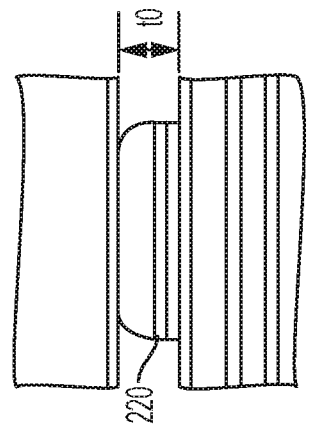
FIG. 3B shows an enlarged view of an electrically conductive gap setting member according to one aspect of the present disclosure.

With reference to FIG. 3B, which shows an enlarged view of the electrically conductive gap setting member 220 according to one aspect of the present disclosure, the height of the electrically conductive gap setting member 220 above the second energy delivery surface 230b defines a minimum distance t0 of the gap 211 between the first and second energy delivery surfaces 230a, 230b near the distal end of the end effector 200 ("the distal gap distance") when the electrically conductive gap setting member 220 is in contact with the first energy delivery surface 230a. In the case where the upper jaw 210a comprises a recession 222, t0 may be the difference between the height of the electrically conductive gap setting member 220 and the depth of the recession 222. The pivot assembly 270 defines a minimum distance t0' between the first and second energy delivery surfaces 230a, 230b near the proximal end of the end effector 200 ("the proximal gap distance").

When a uniform gap is defined between the first energy delivery surface 230a and the second energy delivery surface 230b, the proximal gap distance and the distal gap distance are the same, or at least substantially the same as one another, such that the first and second energy delivery surfaces 230a, 230b are substantially parallel when the jaws 210a and 210b are closed but not deformed. In another aspect, t0<t0', such that the gap gradually becomes narrower from the proximal end to the distal end when the jaws 210a and 210b are closed but not deformed. For example, the difference between t0 and t0' may be 0.002" or more. In other examples, the difference between t0 and t0' may be 0.001", 0.005", 0.006", or any of the values therebetween. Because of the narrower distal gap distance, the degree of compression of the tissue is higher in the distal portion (for example, a ⅓ portion near the distal end), thus providing improved manipulation and sealing in the distal portion.

With reference to FIG. 3C, which shows an enlarged view of the electrically insulative tissue engaging members 240a, 240b, 240c according to one aspect of the present disclosure, the heights t1, t2, t3 of the electrically insulative tissue engaging members 240a, 240b, 240c, respectively, above the second energy delivery surface 230b are less than the distal gap distance t0. For example, the heights t1, t2, t3 of the electrically insulative tissue engaging members 240a, 240b, 240c may be at least 0.002" less than the distal gap distance t0. In other examples, the difference between t0 and the heights t1, t2, t3 may be 0.001", 0.005", 0.006", or any of the values therebetween. Therefore, gap distances g1, g2, g3, respectively, are formed when the upper and lower jaws 210a and 210b are closed. In one aspect, the heights t1, t2, t3 may be substantially the same. In another aspect, t1<t2<t3, for example.

FIG. 4A shows an elevational view of an end effector 400 with an angled configuration, according to one aspect of the present disclosure. Certain parts in the view shown here may be exaggerated for illustration purpose. The end effector 200 of FIG. 1 may be modified according to the end effector 400. The end effector 400 comprises an upper jaw 410a and a lower jaw 410b. The upper jaw 410a comprises a first energy delivery surface 430a, a first distal end 412a and a first proximal end (not shown). The lower jaw 410b comprises a second energy delivery surface 430b, a second distal end 412b and a second proximal end (not shown). As shown in FIG. 4A, the upper jaw 410a is tilted downward near the first distal end 412a, such that the first energy delivery surface 430a comprises a first angled portion 432a positioned at an angle α extending to the first distal end 412a. The lower jaw 410b is also tilted downward near the second distal end 412b, such that the second energy delivery surface 430b comprises a second angled portion 432b positioned at an angle β extending to the second distal end 412b. In one aspect, α may be substantially the same as β, such that the first angled portion 432a and the second angled portion 432b are substantially parallel. In another aspect, α may be greater than β, such that the gap between the first and second angled portions 432a, 432b gradually becomes narrower approaching the first and second distal ends 412a, 412b. The lower jaw 410b may be shorter than the upper jaw 410a, such that the alignment of the first and second distal ends 412a, 412b is preserved.

Figure 4B:
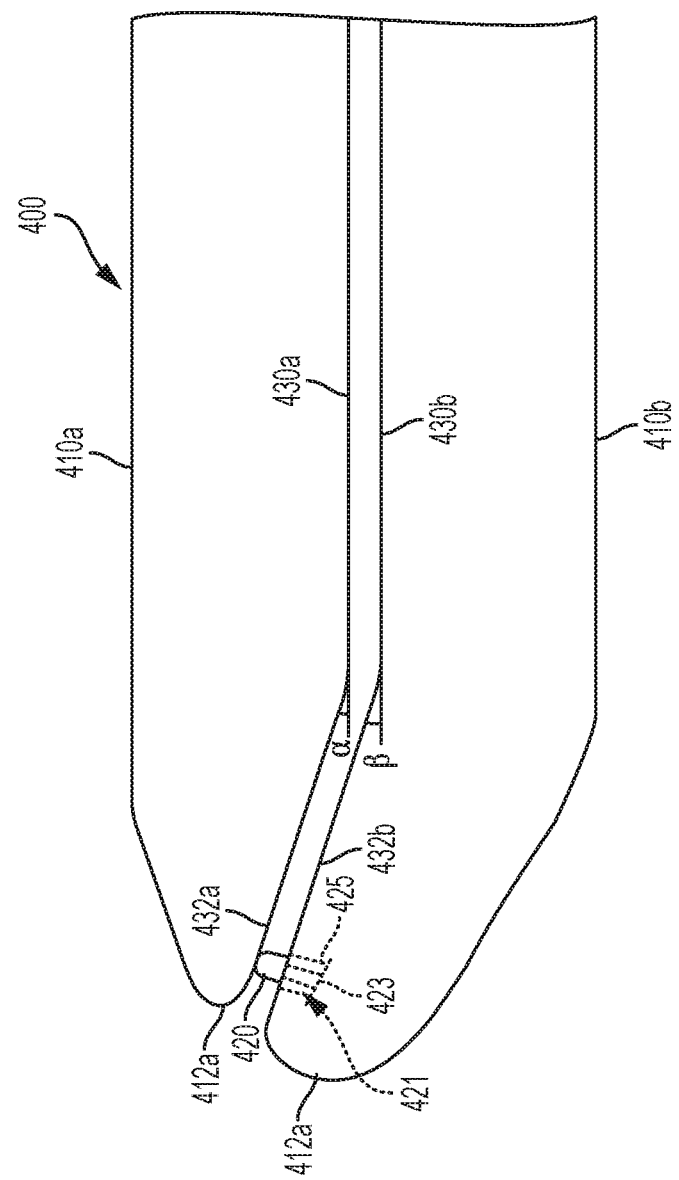
FIG. 4B shows an elevational view of an end effector with an angled configuration, according to one aspect of the present disclosure.

FIG. 4B shows an elevational view of an end effector 400 with an angled configuration, according to one aspect of the present disclosure. The end effector 400 of FIG. 4B is different from that of FIG. 4A in that the jaws 410a, 410b are tilted upward. Accordingly, the lower jaw 410b may be longer than the upper jaw 410a, such that the alignment of the first and second distal ends 412a, 412b is preserved.

The end effector 400 comprises a distal electrically conductive gap setting member 420 similar to the electrically conductive gap setting member 220 in many respects. For example, the electrically conductive gap setting member 420 is located in proximity to the second distal end 412b, as discussed above. The end effector 400 may comprise one or more electrically insulative tissue engaging members (not shown) similar to the electrically insulative tissue engaging members 240 discussed above. This angled configuration provides improved grasping near the distal end.

Referring to FIG. 4A, the electrically conductive gap setting member 420 may be located at a distance away from the edge of the second energy delivery surface 430b at the second distal end 412b. The electrically conductive gap setting member 420 also may be located at a distance away from the lateral edges of the second energy delivery surface 430b. The electrically conductive gap setting member 420 protrudes from the lower jaw 410b and defines a height above the second energy delivery surface 430b. The electrically conductive gap setting member 420 may be substantially in a shape of a post or a cylinder, or any other shape that protrudes from the lower jaw 410b.

The electrically conductive gap setting member 420 may comprise an electrically conductive material such as stainless steel. The electrically conductive gap setting member 420 is arranged so that it is not in contact with the conductive layer (conductive material) of the second energy delivery surface 430b, or in other words, electrically isolated from the conductive material of the second energy delivery surface 430b. For example, the electrically conductive gap setting member 420 may be located near the bottom of the conductive layer on the lower jaw 410b but is separated from the conductive layer. As illustrated in FIG. 4A, the electrically conductive gap setting member 420 extends from a base 423 below the second angled portion 432b of the energy delivery surface 430b, and passes through an aperture 421 defined in the energy delivery surface 430b. A space is provided between the inner periphery 425 of the aperture 421 and the outer periphery of the gap setting member 420 such that the gap setting member 420 does not contact any electrically conductive portion of the energy delivery surface 430b. Although the aperture 421 may have a substantially round shape, the aperture 421 can have any shape as long as the inner periphery of the aperture 421 may not contact any part of the outer periphery of the gap setting member 420.

Figure 5B:
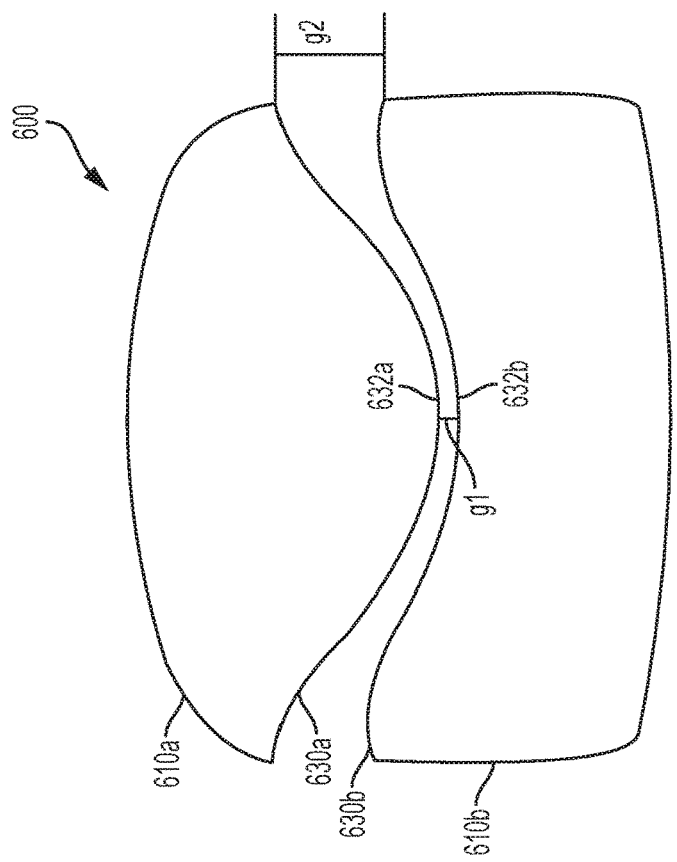
FIG. 5B shows a front view of an end effector with a laterally curved configuration, according to one aspect of the present disclosure.
Figure 5A:
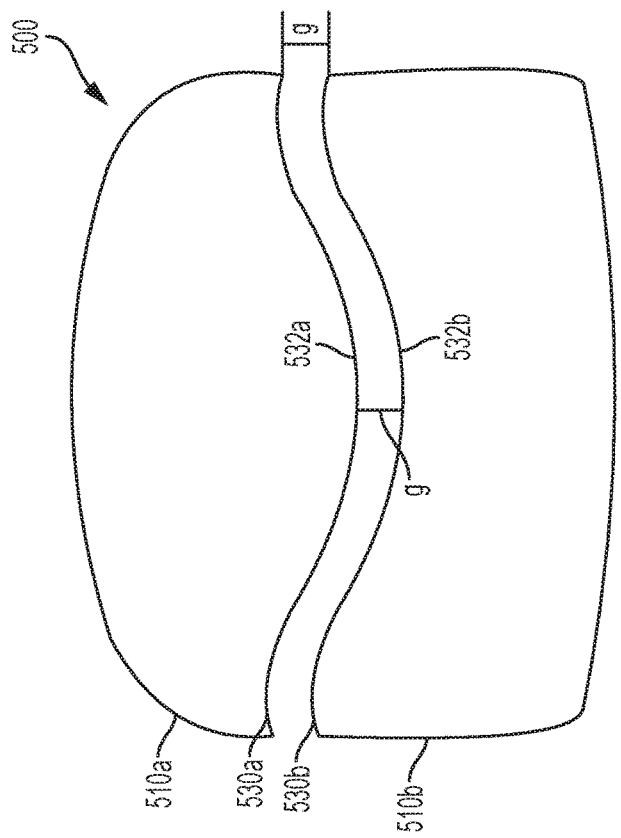
FIG. 5A shows a front view of an end effector with a laterally curved configuration, according to one aspect of the present disclosure.

FIG. 5A shows an end view of an end effector 500 with a laterally curved configuration, according to one aspect of the present disclosure. Lateral cross section means a cross section on a plane substantially perpendicular to a line defined by the distal end and the proximal end. Certain parts in the view shown here may be exaggerated for illustration purpose. The end effector 200 of FIG. 1 may be modified according to the end effector 500. The end effector 500 comprises an upper jaw 510a and a lower jaw 510b. The upper jaw 510a comprises a first energy delivery surface 530a. A lower jaw 510b of the end effector 500 comprises a second energy delivery surface 530b. As shown in FIG. 5A, the first energy delivery surface 530a comprises a first curved portion 532a in the lateral cross section, and the second energy delivery surface 530b comprises a second curved portion 532b in the lateral cross section. The first and second curved portions 532a, 532b each may have a downward curve. In other words, the first curved portion 532a comprises an outward curve, and the second curved portion 532b comprises an inward curve. In other aspects, the first and second curved portions 532a, 532b each may have an upward curve. As shown in FIG. 5A, the first and second curved portions 532a and 532b may have complementary contours. Therefore, the first and second curved portions 532a, 532b define a laterally uniform gap distance g between the first and second energy delivery surfaces. This laterally curved configuration provides improved grasping, and improves the alignment between the upper jaw 510a and the lower jaw 510b.

In one aspect, the first and second curved portions 532a, 532b may be longitudinally uniform. In another aspect, the first and second curved portions 532a, 532b may be longitudinally non-uniform. For example, there may be a longitudinal transition from a non-curved surface to a curved surface. In other aspects, the first and second energy delivery surfaces 530a, 530b each may comprise more than one curved portion in the lateral cross section. For example, a wavy contour is possible.

FIG. 5B shows a lateral cross section view of an end effector 600 with a laterally curved configuration, according to one aspect of the present disclosure. The end effector 600 of FIG. 5B is different from that of FIG. 5A in that the first and second curved portions 632a, 632b define a laterally non-uniform gap distance between the first and second energy delivery surfaces. Specifically, a gap distance g1 at the center is less than a gap distance g2 at lateral edges. This configuration provides focused grasping near the center, and reduces tissue compression near the edges. As shown in FIG. 5B, the first and second curved portions 632a and 632b may have different contours.

In one aspect, the first and second curved portions 632a, 632b may be longitudinally uniform. In another aspect, the first and second curved portions 632a, 632b may be longitudinally non-uniform. For example, there may be a longitudinal transition from a non-curved surface to a curved surface. In other aspects, the first and second energy delivery surfaces 630a, 630b each may comprise more than one curved portion in the lateral cross section. For example, a wavy contour is possible.

FIGS. 6A and 6B each show lateral cross section views of end effector 500' and 600' which are similar in many respects to the end effectors 500 and 600, respectively. The end effectors of FIGS. 6A and 6B are different from those of FIGS. 5A and 5B in that they further comprise distal electrically conductive gap setting members 520 and 620, respectively, which are similar to the electrically conductive gap setting member 220 discussed above. The electrically conductive gap setting members 520 and 620 are positioned in proximity to distal ends of their respective end effectors.

As shown in FIG. 6A, the electrically conductive gap setting member 520 is located at a laterally central position with respect to the energy delivery surfaces 530a and 530b. The electrically conductive gap setting member 520 extends from the jaw 510b toward the jaw 510a. Alternatively, an electrically conductive gap setting member may extend from the jaw 510a toward the jaw 510b. The electrically conductive gap setting member 520 extends from a base 523 below the curved portion 532b of the energy delivery surface 530b, and passes through an aperture 521 defined in the energy delivery surface 530b. A space is provided between the inner periphery of the aperture 521 and the outer periphery of the gap setting member 520 such that the gap setting member 520 does not contact any electrically conductive portion of the energy delivery surface 530b. Although the aperture 521 may have a substantially round shape, the aperture 521 can have any shape as long as the inner periphery of the aperture 521 may not contact any part of the outer periphery of the gap setting member 520. The height of the electrically conductive gap setting member 520 above or beyond the energy delivery surface 530b defines the uniform gap distance g between the energy delivery surfaces 530a, 530b in a closed position.

As shown in FIG. 6B, the electrically conductive gap setting member 620 is located at a laterally central position with respect to the energy delivery surfaces 630a and 630b. The electrically conductive gap setting member 620 extends from the jaw 610b toward the jaw 610a. Alternatively, an electrically conductive gap setting member may extend from the jaw 610a toward the jaw 610b. The electrically conductive gap setting member 620 extends from a base 623 below the second curved portion 632b of the energy delivery surface 630b, and passes through an aperture 621 defined in the energy delivery surface 630b. A space is provided between the inner periphery of the aperture 621 and the outer periphery of the gap setting member 620 such that the gap setting member 620 does not contact any electrically conductive portion of the energy delivery surface 630b. Although the aperture 621 may have a substantially round shape, the aperture 621 can have any shape as long as the inner periphery of the aperture 621 may not contact any part of the outer periphery of the gap setting member 620. The height of the electrically conductive gap setting member 620 above or beyond the energy delivery surface 630b defines the minimum gap distance g1 between the energy delivery surfaces 630a, 630b in a closed position, and the maximum gap distance g2 between the energy delivery surfaces 630a, 630b in the closed position.

Figure 7:
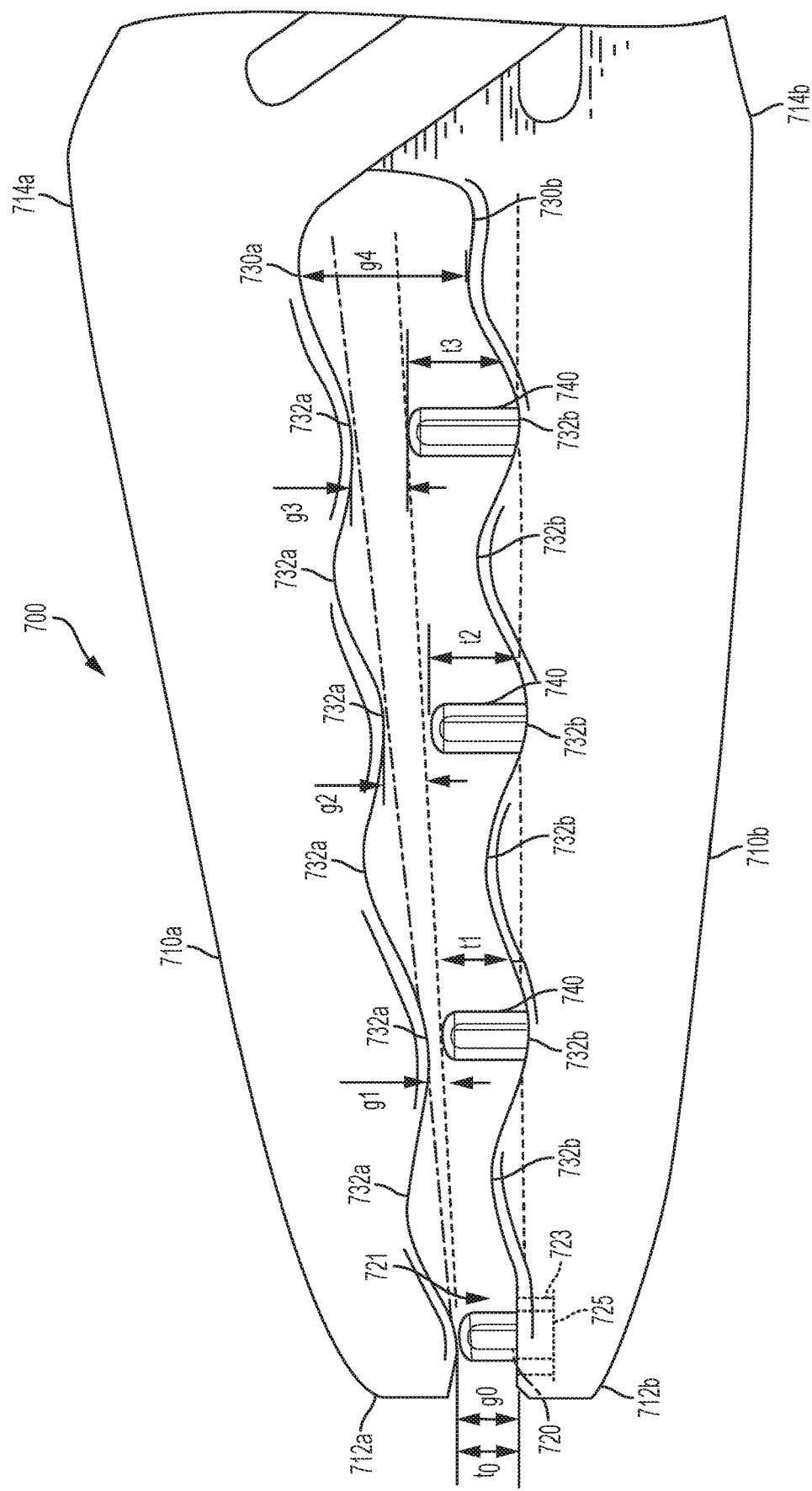
FIG. 7 shows a longitudinal cross section view of an end effector with a longitudinally curved configuration, according to one aspect of the present disclosure.

FIG. 7 shows a longitudinal cross section view of an end effector 700 with a longitudinally curved configuration, according to one aspect of the present disclosure. Longitudinal cross section means a cross section on a plane substantially parallel to a line defined by the distal end and the proximal end and substantially parallel to a line pointing from upper jaw 710a to lower jaw 710b. Certain parts in the view shown here may be exaggerated for illustration purpose. The end effector 200 of FIG. 1 may be modified according to the end effector 700. The end effector 700 comprises an upper jaw 710a and a lower jaw 710b. The upper jaw 710a comprises a first energy delivery surface 730a. The lower jaw 710b comprises a second energy delivery surface 730b. As shown in FIG. 7, the first energy delivery surface 730a comprises at least one first curved portion 732a in the longitudinal cross section, and the second energy delivery surface 730b comprises at least one second curved portion 732b in the longitudinal cross section. The first and second curved portions 732a, 732b each may have an upward curve or a downward curve. For example, as shown in FIG. 7, a plurality of the first curved portions 732a may form a first energy delivery surface 730a having a wavy contour, and a plurality of the second curved portions 732b may form a second energy delivery surface 730b having a complimentary wavy contour. This longitudinally curved configuration of FIG. 7 provides improved grasping.

The end effector 700 includes a distal electrically conductive gap setting member 720 similar to the electrically conductive gap setting member 220 discussed above. The electrically conductive gap setting member 720 has a height t0 above the second energy delivery surface 730b. The electrically conductive gap setting member 720 extends from a base 723 below the energy delivery surface 730b in proximity to the distal end 712b, and passes through an aperture 721 defined in the energy delivery surface 730b. A space is provided between the inner periphery 725 of the aperture 721 and the outer periphery of the gap setting member 720 such that the gap setting member 720 does not contact any electrically conductive portion of the energy delivery surface 730b. Although the aperture 721 may have a substantially round shape, the aperture 721 can have any shape as long as the inner periphery of the aperture 721 may not contact any part of the outer periphery of the gap setting member 720.

As shown in FIG. 7, the electrically conductive gap setting member 720 defines a gap distance g0 between the energy delivery surfaces 730a, 730b in proximity to distal ends 712a, 712b of the jaws 710a in the closed position that is equal to the height t0. A gap distance g4 defined between the energy delivery surfaces 730a, 730b in proximity to proximal ends 714a, 714b of the jaws 710a, 710b may be greater than the gap distance g0. In other aspects, a uniform gap distance is possible.

The end effector 700 also includes one or more electrically insulative tissue engaging member 740 similar to the electrically insulative tissue engaging members 240 discussed above. The electrically insulative tissue engaging members 740 shown FIG. 7 may have heights above the second energy delivery surface 730b t1, t2, and t3, and may form gaps g1, g2, g3, respectively, from the first energy delivery surface 730a. As shown in FIG. 7, t1<t2<t3, and g1<g2<g3, to adapt to a non-parallel or non-uniform gap between the jaws 710a, 710b in the closed position.

What is claimed is:
1. An end effector for an electrosurgical instrument, comprising:
   a first jaw comprising a first energy delivery surface, a first distal end, and a first proximal end;

a second jaw comprising a second energy delivery surface, a second distal end, and a second proximal end, wherein the first and second jaws are pivotally coupled at the first and second proximal ends, such that at least one of the first and second jaws is configured for pivotal movement between a closed position where the first and second distal ends are in proximity and the first and second energy delivery surfaces face each other, and an open position where the first and second distal ends are separated apart, the first energy delivery surface comprises a first curved portion that is outwardly curved, and the second energy delivery surface comprises a second curved portion that is inwardly curved; and an electrically conductive member protruding from the first jaw or second jaw and configured to contact a conductive surface of the other one of the first jaw or second jaw in the closed position, wherein the electrically conductive member is in proximity to the first and second distal ends in the closed position, and wherein the electrically conductive member defines a minimum gap distance between the first energy delivery surface and the second energy delivery surface in the closed position.

2. The end effector of claim 1, wherein the first curved portion and the second curved portion are curved in a lateral cross section.

3. The end effector of claim 2, wherein the first curved portion and the second curved portion define a gap between the first and second energy delivery surfaces with a laterally uniform gap distance.

4. The end effector of claim 2, wherein the first curved portion and the second curved portion define a gap between the first and second energy delivery surfaces with a laterally non-uniform gap distance, wherein a gap distance at lateral edges is greater than a gap distance at center.

5. The end effector of claim 2, wherein the first curved portion and the second curved portion are longitudinally uniform.

6. The end effector of claim 2, wherein the first energy delivery surface comprises a longitudinal transition from the first curved portion to a first non-curved portion, and the second energy delivery surface comprises a longitudinal transition from the second curved portion to a second non-curved portion.

7. The end effector of claim 1, wherein the first curved portion and the second curved portion are curved in a longitudinal cross section.

8. The end effector of claim 7, wherein the first energy delivery surface comprises a third curved portion curved in the longitudinal cross section, and the second energy delivery surface comprises a fourth curved portion curved in the longitudinal cross section.

9. The end effector of claim 8, wherein the first and third curved portions define a first wavy contour, and the second and fourth curved portions define a second wavy contour complimentary to the first wavy contour.

10. The end effector of claim 8, wherein the first and third curved portions and the second and fourth curved portions define a gap between the first and second energy delivery surfaces with longitudinally non-uniform gap distance, wherein the gap comprises a proximal gap distance between the first and second energy delivery surfaces and a distal gap distance between the first and second energy delivery surfaces, and wherein the proximal gap distance is greater than the distal gap distance.

11. The end effector of claim 8, wherein the first and third curved portions and the second and fourth curved portions define a gap between the first and second energy delivery surfaces with longitudinally uniform gap distance.

12. The end effector of claim 1, wherein the first curved portion and the second curved portion are curved in a lateral cross section, and the first curved portion and the second curved portion are curved in a longitudinal cross section.

13. The end effector of claim 1, further comprising at least one electrically insulative member protruding from the first or second energy delivery surface.

14. An end effector for an electrosurgical instrument, comprising:

an upper jaw comprising a first energy delivery surface, a first distal end, and a first proximal end;

a lower jaw comprising a second energy delivery surface, a second distal end, and a second proximal end, wherein the upper and lower jaws are pivotally coupled at the first and second proximal ends, such that at least one of the upper and lower jaws is configured for pivotal movement between a closed position where the first and second distal ends are in proximity and the first and second energy delivery surfaces face each other, and an open position where the first and second distal ends are separated apart, the first energy delivery surface comprises a first angled portion extending to the first distal end, the first angled portion tilted at a first angle, the second energy delivery surface comprises a second angled portion extending to the second distal end, the second angled portion tilted at a second angle; and an electrically conductive member protruding from the upper jaw or lower jaw and configured to contact a conductive surface of the other one of the upper jaw or lower jaw in the closed position, wherein the electrically conductive member is in proximity to the first and second distal ends in the closed position, and wherein the electrically conductive member defines a minimum gap distance between the first energy delivery surface and the second energy delivery surface in the closed position.

15. The end effector of claim 14, wherein the first and second angled portions are tilted upward.

16. The end effector of claim 15, wherein the lower jaw is longer than the upper jaw.

17. The end effector of claim 14, wherein the first and second angled portions are tilted downward.

18. The end effector of claim 17, wherein the upper jaw is longer than the lower jaw.

19. The end effector of claim 14, wherein the electrically conductive member defines a gap between the first and second energy delivery surfaces that is narrowing towards the first and second distal ends.

* * * * *